United States Patent
Dahlin et al.

(10) Patent No.: US 6,685,759 B2
(45) Date of Patent: Feb. 3, 2004

(54) CASCADE IMPACTOR AND JET PLATE FOR SAME

(75) Inventors: Robert S. Dahlin, Birmingham, AL (US); William E. Farthing, Pinson, AL (US); Edward C. Landham, Jr., Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 10/193,384

(22) Filed: Jul. 11, 2002

(65) Prior Publication Data

US 2003/0079524 A1 May 1, 2003

Related U.S. Application Data

(62) Division of application No. 09/670,794, filed on Sep. 25, 2000, now abandoned.

(51) Int. Cl.[7] .............................. B01D 45/08; G01N 1/22
(52) U.S. Cl. ............................ 55/465; 55/464; 96/147; 96/154; 73/863.22; 73/28.05
(58) Field of Search ..................... 73/863.21, 863.22, 73/863.85, 28.04, 28.05, 28.06; 55/464, 465; 96/108, 134, 136, 139, 147, 152, 154

(56) References Cited

U.S. PATENT DOCUMENTS

| | | | |
|---|---|---|---|
| 2,434,389 A | 1/1948 | Breth et al. ................ 209/133 |
| 3,001,914 A | 9/1961 | Anderson .............. 73/28.05 X |
| 3,528,273 A | 9/1970 | Elton et al. |
| 3,693,457 A | 9/1972 | Pilat ...................... 73/28.05 X |
| 3,771,291 A | 11/1973 | Klingler ................... 55/391 X |
| 3,795,135 A | 3/1974 | Andersen .................. 73/28.06 |
| 3,825,000 A | 7/1974 | Huggins ................. 128/200.4 |
| 3,983,743 A | 10/1976 | Olin et al. ................. 73/28.06 |
| 4,133,202 A | 1/1979 | Marple .................. 73/865.5 X |
| 4,189,937 A | 2/1980 | Nelson ...................... 73/28.06 |
| 4,211,116 A | 7/1980 | Pilat et al. ............... 73/863.22 |
| 4,274,846 A | 6/1981 | Smith ....................... 55/319 X |
| 4,340,399 A | 7/1982 | Luthra et al. ................. 95/133 |
| 4,387,603 A | 6/1983 | Nelson .................... 73/863.22 |
| 4,606,232 A | 8/1986 | Prodl ...................... 73/863.23 |
| 4,796,475 A | 1/1989 | Marpel .................... 73/863.22 |
| 4,941,899 A | 7/1990 | Liu ...................... 73/863.23 X |
| 5,173,263 A | 12/1992 | Lee .............................. 422/88 |
| 5,308,483 A | 5/1994 | Sklar et al. ................. 210/232 |
| 5,404,762 A | 4/1995 | Rodgers et al. .......... 73/863.25 |
| 5,498,271 A | 3/1996 | Marple et al. ................ 55/321 |
| 5,533,406 A | 7/1996 | Geise ...................... 73/863.22 |
| 5,970,781 A | 10/1999 | Hiss, III et al. ........... 73/28.01 |
| 5,992,974 A | 11/1999 | Miyata ........................ 347/47 |
| 6,103,534 A | 8/2000 | Stenger et al. ............. 73/28.01 |
| 6,151,970 A | 11/2000 | Shih et al. ............... 73/863.22 |
| 6,431,014 B1 * | 8/2002 | Liu et al. ................. 73/863.22 |
| 6,435,043 B1 * | 8/2002 | Ferguson et al. ........ 73/863.22 |

FOREIGN PATENT DOCUMENTS

| | | | |
|---|---|---|---|
| GB | 2254024 A | 9/1992 | ............. 209/139.2 |
| JP | 0047247 | 7/1967 | |

* cited by examiner

Primary Examiner—Thomas P. Noland
(74) Attorney, Agent, or Firm—Needle & Rosenberg, P.C.

(57) ABSTRACT

A sampling system and method for sampling particulate matter from a high-temperature, high-pressure gas stream. A cyclone sampler for use at high temperatures and pressures, and having threadless sacrificial connectors is disclosed. Also disclosed is an improved cascade impactor including jet plates with integral spacers, and alignment features provided for aligning the jet plates with their associated collection substrates. An activated bauxite alkali collector is disclosed, and includes an alumina liner. The sampling system can be operated remotely or locally, and can be permanently installed or configured as a portable system.

2 Claims, 26 Drawing Sheets

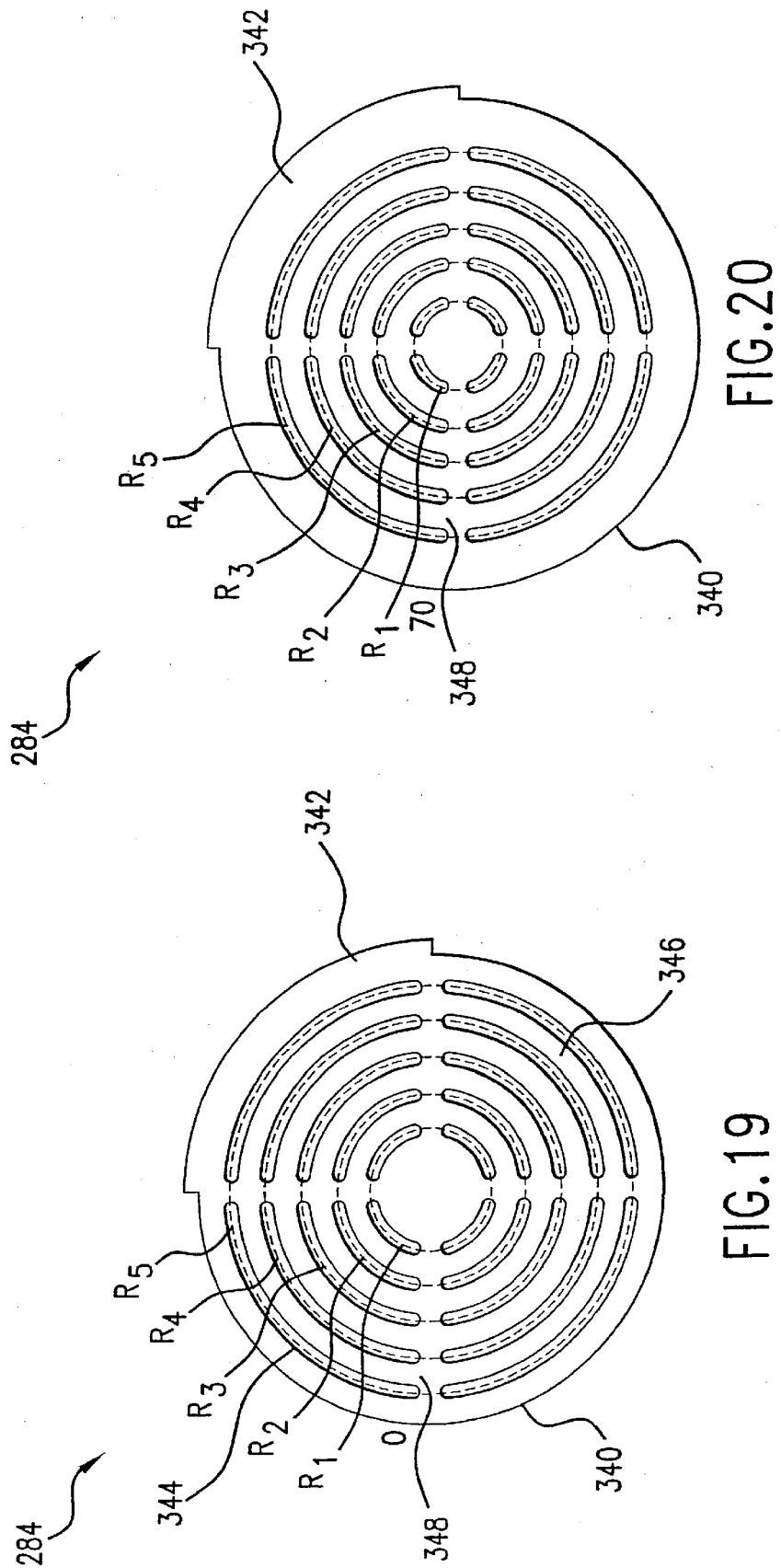

CASCADE IMPACTOR AND JET PLATE FOR SAME

This application is a divisional of, and claims the benefit of, Application Ser. No. 09/670,794, filed Sep. 25, 2000 now abandoned, which application is hereby incorporated herein in its entirety by reference.

This invention was made with government support under a cooperative agreement entered into with the U.S. Department of Energy, No. DE-FC21-90MC25140. The government has certain rights in the invention.

BACKGROUND OF THE INVENTION

1. Field of the Invention

The present invention relates generally to particulate sampling systems, and more specifically to devices, methods and systems for isokinetic sampling of particulate matter, in-situ, from a high-temperature and/or high-pressure gas stream.

2. Description of Related Art

Various industrial processes generate gas streams containing particulate matter. For example, coal-based power generation technologies produce particulate-loaded streams of process gas. The gas streams are often filtered to remove entrained particulate matter prior to release to the atmosphere to reduce emissions, and/or prior to introduction to process equipment that may be damaged by the particulate matter. For example, particulate control devices (PCDs), such as ceramic barrier filters or granular bed filters can be utilized to remove particulate matter from process gasses produced by coal gasification and combustion prior to their use in a turbine or fuel cell to generate electricity in a power generation plant. Gas turbines utilized in power generation typically require particulate loading in the gas supply stream of less than 20 ppmw (parts per million by weight) or less than 24 mg/m$^3$, with less than one percent of the particulate matter being larger than 10 microns ($\mu$m). See McClung, et al., "Design and Operating Considerations for an Advanced PFBC Plant at Wilsonville", in *Proceedings of the 13th International Conference on Fluidized-Bed Combustion*, Vol. 1, pp. 107–115, Published by American Society of Mechanical Engineers, 1995. Increasingly stringent environmental protection regulations typically limit particulate emissions to the environment to 30 ppmw or less, and advanced emission control systems may enable particulate removal to as low as 0.2 ppmw or less.

The characteristics of a gas stream containing particulate matter often must be determined by sampling the gas stream. Sampling may be required to determine the overall quantity of particulate matter in a given volume of gas, to determine the portion of the particulate matter that falls within one or more particle size ranges, and/or to determine various characteristics of the particulate matter or the overall gas stream (such as, for example, chemical content, pH, temperature, pressure, flowrate, etc.). A variety of sampling devices have been developed for these purposes. For example, extractive sampling techniques remove a portion of the particulate-laden gas from the gas stream for processing and/or analysis in an external sampler device. Extractive sampling suffers a number of disadvantages. For example, the particulate properties may be altered during extraction. Various components of the gas stream, such as, for example, alkali or tar vapors in the gas stream, may condense during extraction. To minimize the adverse effects of sample gas cooling, extractive sampling lines must be heat traced, and expensive, high-temperature isolation valves must be used. Unfortunately, these complicated and expensive heat tracing systems are only partially successful in minimizing condensation of gas stream components, and add considerably to the expense of the sampler. In addition, collisions of the particles with one another and with the walls of the sampling lines during extraction alter the particulate content and sizing. See Anand, et al., "Optimization of Aerosol Penetration Through Transport Lines," Aerosol Science and Technology, Vol. 16, pp. 105–112 (1992). Thus, in-situ, isokinetic sampling of the gas stream has been found to be desirable. With an in-situ sampling system, it is not necessary to heat trace the external portion of the system, and it is possible to use less-expensive, low-temperature isolation valves. By allowing the use of less-expensive valves, the in-situ sampling system can be a more cost-effective means of sampling and provides more representative samples when compared to an extractive sampling system.

Enabling in-situ, isokinetic sampling, however, presents a number of challenges. The size of sampling devices for in-situ sampling is often severely constrained by the associated process equipment. For example, in situ sampling of a gas stream flowing within a twelve-inch (12") process pipe typically requires that the sampler size be considerably less than twelve inches, and not present an unacceptable flow restriction within the pipe. Additional constraints on the size and configuration of a sampling device may result from the sampling technique. For example, a sampler may need to be specially configured for sampling at or near the wall of a process pipe, or at the midpoint of the flow. Access limitations and safety concerns also may dictate the need for remote control of the sampling equipment, and the need for seals, purge systems, and other substantial means for isolating the gas stream from the external environment during sampling.

Further challenges to the successful development of in-situ, isokinetic sampling are presented by the characteristics of the particulate-laden gas stream being sampled. For example, recent and ongoing developments in advanced technologies for power generation, such as coal-based advanced pressurized fluidized-bed combustion (APFBC) and integrated gasification combined cycle (IGCC) processes, result in the need for sampling of process gas streams at very high pressures, often up to and exceeding 150–400 psia (1.0–2.8 MPa), and at very high temperatures, often up to and exceeding 600–1600° F. (320–870° C.). The gas streams to be sampled may further contain one or more highly corrosive and/or abrasive constituents.

Previously-known sampling devices and methods are typically inadequate for sampling particulate-laden gas streams at such extreme conditions. For example, known cascade impactors for sampling particulate, such as those shown and described in U.S. Pat. Nos. 3,001,914; 3,693,457; and 3,795,135, which are hereby incorporated by reference herein, often suffer from galling, fusion of contacting components, deterioration of materials, and other damage at extreme conditions. For example, previously known samplers typically include separate spacer elements between adjacent stages, and/or separate spacer elements between the jet plate and associated collection substrate of a single stage. These spacer elements are commonly in the form of cross-shaped supports or rings that are placed between adjacent components of an impactor during assembly. These spacer elements may undergo fusion or material transfer by galling with adjacent components at elevated temperatures, potentially resulting in analysis errors. In addition, the numerous components of a typical impactor render assembly and disassembly time consuming and subject to error or damage.

In addition, previously-known cyclone samplers at best provide limited utility in high-temperature, high-pressure sampling applications. For example, a prior art five-stage cyclone assembly included threaded connections on each of its five cyclone separators, which require disassembly by unthreading these connections to access and analyze the particulate matter collected therein. Threaded connections typically present on such samplers have been found to seize due to galling from exposure to high-temperature gas streams. In addition, the cyclone separators of the conventional five-stage cyclone assembly are laid out on the manifold in a longitudinally-spaced arrangement that results in an overall sampler length that has been found unacceptable for in-situ sampling in certain process vessels. Still further, the configuration and materials of construction of the conventional five-stage cyclone assembly provide inadequate structural rigidity, and the assembly may deform under its own weight at high temperatures.

Through considerable experimentation, applicants have discovered advantages in combining two or more devices into a single sampling system, thereby overcoming constraints imposed by in-situ, isokinetic sampling at high-temperature and high-pressure. For example, a cyclone sampler or a cascade impactor can be operated in series with an alkali vapor collector, as described in greater detail elsewhere herein, with the outlet of the cyclone sampler or cascade impactor communicating with the inlet of the alkali collector. Previously-known sampling devices are generally unsuited for use in combination in this manner. For example, the combination of an alkali collector with the conventional five-stage cyclone assembly would require substantial modification, and would result in an unacceptable sampler length.

Thus it can be seen that needs exist for improved sampling devices, methods and systems. It is to the provision of improved sampling devices, methods and systems that the present invention is primarily directed.

SUMMARY OF THE INVENTION

The present invention provides a system, method, and various associated devices for collecting and sampling particulate matter and other characteristics of a fluid. The various aspects of the present invention can be implemented, via remote and/or local control, by a sampling system that may be permanently installed to fluid-handling equipment, or by a portable sampling system designed for temporary and removable attachment to fluid-handling equipment.

By way of example, and without limitation to other applications, the present invention enables isokinetic in-situ sampling of particulate matter from high-temperature, high-pressure process gas streams generated in power-generation facilities. The present invention allows determination of fluid characteristics, such as particulate loadings, particle size distributions, and alkali vapor content. Separate samples may be taken upstream and downstream of a PCD, sequentially or simultaneously, to evaluate the particulate-removal performance of the PCD. Sampling can be conducted for a number of reasons, such as regulatory compliance, to prevent equipment damage, or to monitor for performance degradation or failure of a PCD.

The present invention provides a compact sampler suited for use in confined spaces, and can be configured for remote and/or local control and monitoring. Optionally, the sampling system of the present invention can be configured as a portable system adaptable for use with a variety of fluid handling vessels. Alternatively, the system can be permanently installed. Multiple devices can be combined in a single sampling system according to preferred forms of the present invention. For example, an alkali collector can be coupled with a particulate sampling device, with the inlet of the alkali collector receiving fluid discharged from the particulate sampling device. The particulate sampling device can take the form of a cyclone separator, a cascade impactor, or a total-mass sampler according to various forms of the present invention. For example, a cyclone sampler may be advantageously employed upstream of a PCD for collection and analysis of the relatively higher particulate loading in the fluid stream prior to treatment by the PCD, and a cascade impactor or a total-mass sampler employed downstream of the PCD where particulate loadings are relatively lower, thereby obtaining the benefit of the collection capacity of the cyclone sampler and the sensitivity of the cascade impactor and the total-mass sampler.

Briefly described, one aspect of the present invention provides a cyclone sampler for sampling particulate matter from a fluid. The cyclone sampler preferably includes a manifold having at least one conduit for communicating a stream of fluid containing particulate matter. The sampler preferably also includes at least one cyclone subassembly for collecting a sample of particulate matter. Sacrificial connection means are preferably provided for releasably connecting the cyclone subassembly to the manifold. The provision of the sacrificial connection means and the elimination of threaded connections provides improved high-temperature performance, reducing or eliminating heat-induced damage and/or fusion of components.

The cyclone subassembly preferably includes a housing having a first end comprising an entry port and a second end comprising an access opening. The cyclone subassembly preferably also includes a generally conical cyclone chamber within the housing, having an inlet and an outlet, and bounded by a sloping sidewall. The cyclone subassembly preferably also includes a collection cup communicating with the outlet of the cyclone chamber and with the access opening of said housing. Preferably also included is a cap for closing the access opening, and sacrificial connection means for retaining the cap within the access opening.

In still another aspect, the present invention provides a cascade impactor for analyzing particulate matter in a gas stream. The cascade impactor preferably includes a housing having an inlet for receiving a gas flow, a flowpath communicating the gas flow through the housing, and an outlet for discharging the gas flow. The cascade impactor preferably also includes at least one jet plate within the flow path. The cascade impactor preferably also includes at least one collection substrate, each collection substrate being within the flow path downstream of an associated jet plate, each collection substrate having at least one slot therethrough and at least one impact surface. Each jet plate and each collection substrate preferably also include alignment tabs, which cooperate with alignment means for aligning the alignment tab of each said jet plate with the alignment tab of the associated collection substrate. The alignment tabs make assembly and disassembly of the impactor easier and faster, and reduce the possibility of incorrect assembly.

Each jet plate for the cascade impactor preferably includes a body portion having a first surface, a second surface, and at least one opening extending therethrough. The jet plate preferably also includes an integral spacer depending from the first surface. The integral spacer can take the form of, for example, a circumferential lip, and/or first and second diametrical ribs. The provision of the integral spacers facilitates assembly and disassembly, and reduces the possibility of incorrect assembly. The susceptibility to heat-induced damage and resultant errors in analysis are typically also reduced by the provision of the integral spacers. Each collection substrate for the cascade impactor preferably has at least one passage therethrough, at least one impact surface, and an alignment tab.

In yet another aspect, the present invention provides a total-mass sampler for analyzing particulate matter in a gas stream. The total-mass sampler preferably includes a housing having an inlet for receiving a gas flow, a flowpath communicating the gas flow through the housing, and an outlet for discharging the gas flow. The total-mass sampler preferably also includes a particle collection filter within the flow path. The total-mass sampler preferably also includes a perforated metal plate downstream of the particle collection filter to support the filter. The exemplified total-mass sampler does not split the sample into different particle-size fractions and is capable to collecting samples that are larger than the samples collected in either the exemplified cyclone sampler or the exemplified cascade impactor.

In another aspect, the present invention provides an alkali vapor collector for analyzing an alkali vapor content of a gas stream. The alkali vapor collector preferably includes a housing for attachment to an external support, the housing having an inlet for receiving a sample of a fluid. The alkali vapor collector preferably also includes a quantity of activated bauxite or activated alumina disposed within the housing and exposed to the sample of fluid, and a fluid-impervious liner between the housing and the bauxite or alumina. The provision of the liner advantageously reduces damage to the housing that might otherwise result from contact with alkali-bearing vapors and/or condensate. The provision of the liner also advantageously minimizes loss of alkali vapor on the inner metal surfaces of the housing, which could lead to erroneous measurements of the alkali vapor content of the gas.

These and other features and advantages of preferred forms of the present invention are described herein with reference to the drawing figures.

BRIEF DESCRIPTION OF THE FIGURES OF THE DRAWINGS

The accompanying drawings, which are incorporated in and constitute a part of this specification, illustrate several embodiments of the invention and together with the description, serve to explain the principals of the invention.

FIG. 19 shows a plan view of a first embodiment of a collection substrate.

FIG. 20 shows a plan view of a second embodiment of the collection substrate.

DETAILED DESCRIPTION

The present invention is more particularly described in the following examples that are intended to be illustrative only since numerous modifications and variations therein will be apparent to those skilled in the art. As used in the specification and in the claims, the singular form "a," "an" and "the" include plural referents unless the context clearly dictates otherwise.

Figure 1:
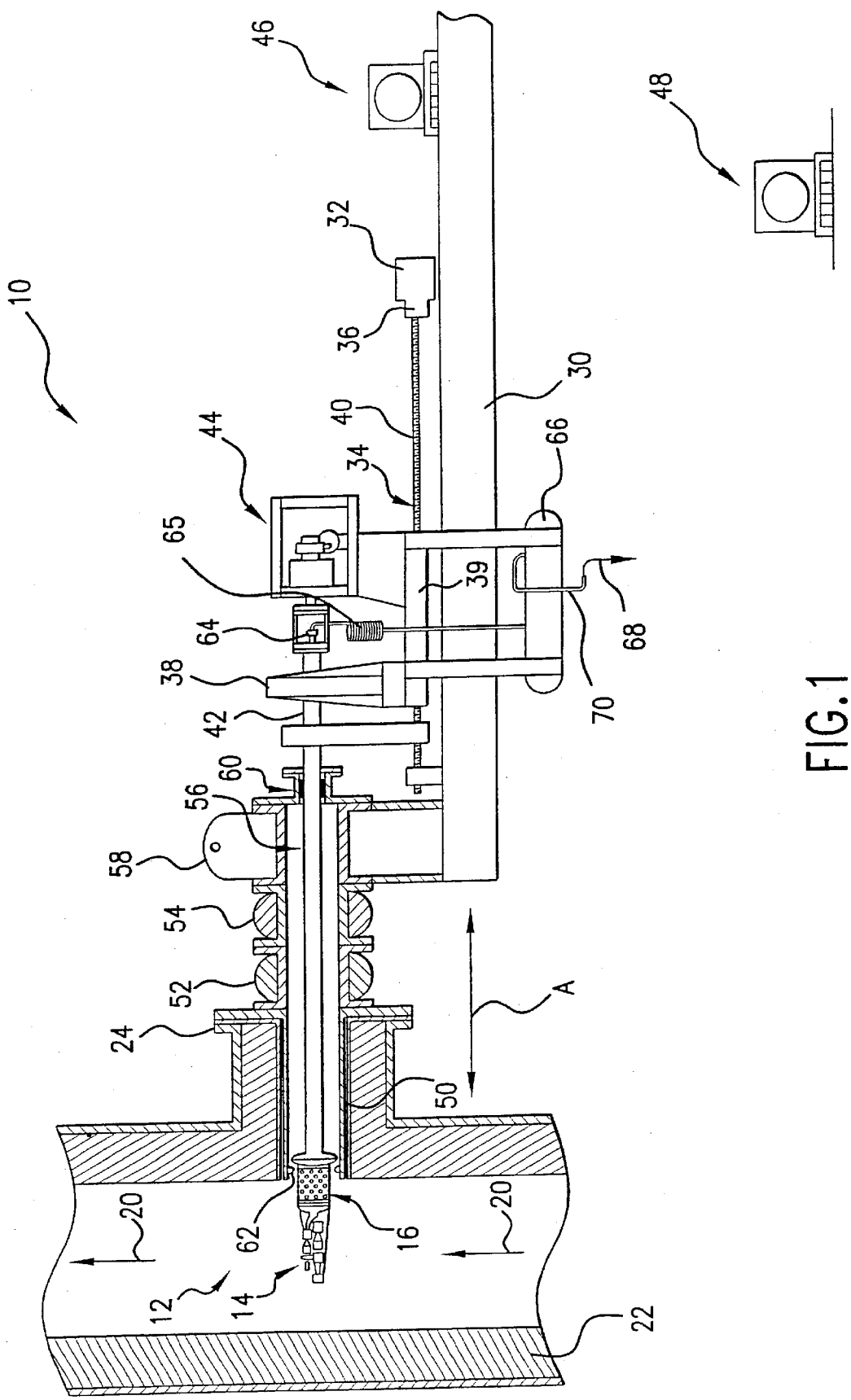
FIG. 1 shows a schematic view of a sampling system according to a preferred embodiment of the present invention.
Figure 2:
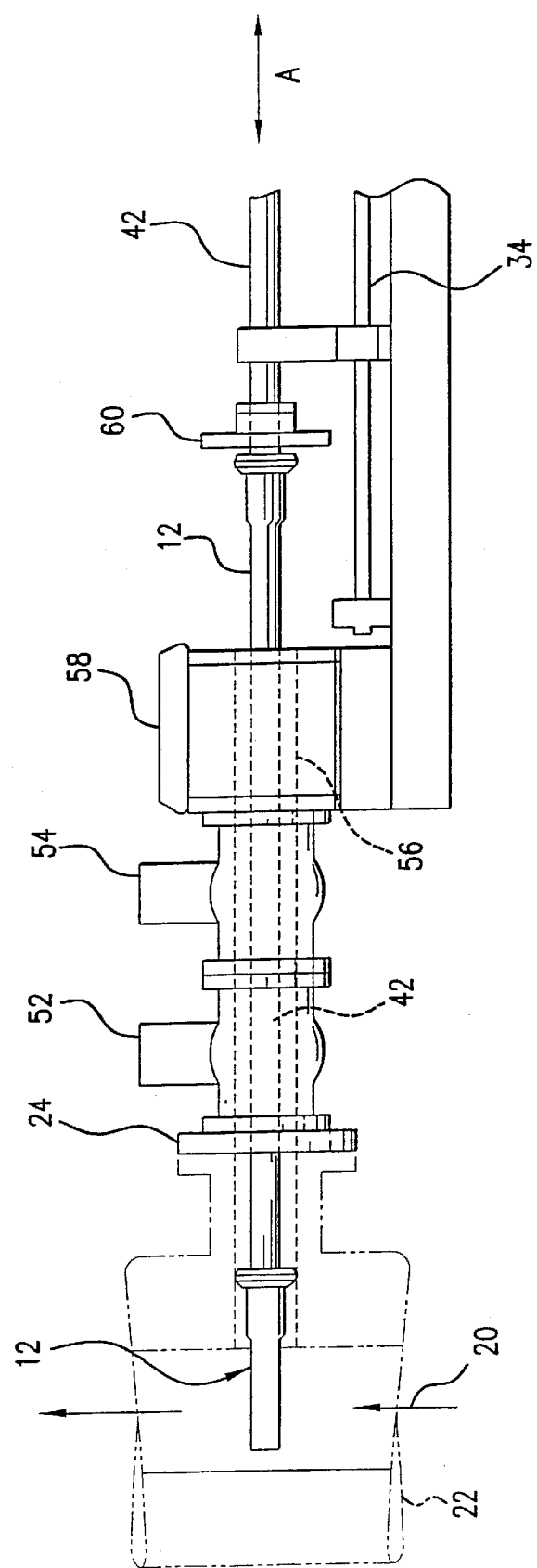
FIG. 2 shows a partial schematic view of the sampling system of FIG. 1, showing the sampling device in a sampling position and in a servicing position.

Referring now to the drawing figures, wherein like reference numerals represent like parts throughout, preferred embodiments of the present invention will now be described. FIG. 1 shows a sampling system 10 according to a preferred embodiment of the present invention. The sampling system 10 comprises a sampling device 12, comprising a particulate sampling means 14 or, in combination, a particulate sampling means 14 and an alkali vapor collector 16. Temperature sensors, pressure sensors and/or other means for monitoring fluid characteristics (not shown) can optionally be included. In the embodiment depicted in FIGS.

1 and 2, the particulate sampling means 14 comprises a cyclone separator, and in alternate embodiments, the particulate sampling means 14 can comprise a cascade impactor or other sampler, such as, for example, a total-mass sampler. In the preferred embodiment, the discharge from the particulate sampling means 14 is communicated into the inlet of the alkali vapor collector 16, whereby the collection of particulate matter by the particulate sampling means 14 advantageously eliminates particulate loading in the alkali vapor collector 16, thereby eliminating fouling or clogging and allowing accurate measurement of the alkali vapor content of the sampled gas.

The sampling device 12 is preferably advanced into and retracted from contact with a fluid 20, such as a gas flowing within a process pipe 22 or other vessel or containment. A pipe flange 24 or other portal is preferably provided for access into the interior of the pipe 22. Cooperating control and isolation systems are preferably provided to effect advancement and retraction of the sampling device 12, and to isolate against escape of the fluid 20. A support structure 30 is preferably provided adjacent the flange 24 or other access portal, for mounting, supporting or attaching components of the control system and the isolation system, and to provide personnel access.

In a preferred embodiment, the control system comprises actuation means, such as a stepper motor 32 driving a screw actuator 34 through a gearbox 36, for advancing and retracting the sampling device 12, and for selectively positioning the sampling device within a vessel, i.e, within the fluid stream. The stepper motor preferably comprises a built-in encoder to ensure positive and accurate positioning of the sampling device 12. Suitable stepper motors, gearboxes, screw actuator mechanisms, and stepper drives are known in the art and are exemplified by the Empire Magnetics Model PT-U23-R Stepper Motor suitable for use in hazardous environments with built-in resolver/encoder, the Bayside Model NE42-005 5:1 Gearbox, the Thomson Industries Model 2EB24FTBJ-S Superslide screw actuator mechanism, and the Parker Compumotor Model AT6400 Controller and Parker Compumotor Model S8 Microstepping Drive.

A carriage 39, carrying a draw yoke 38, is driven along a linear bearing rail 40 by engagement with the screw actuator 34. The draw yoke 38 engages a probe 42, which carries the sampling device 12 at its distal end, to linearly advance and retract the probe 42 and attached sampling device in an axial direction A. The draw yoke 38 is preferably coupled with the probe 42 through a thrust bearing, which allows the draw yoke to impart forces to advance and retract the probe 42, but permitting rotation of the probe 42 about its axis. A rotation means 44, for example a stepper motor or a pneumatic piston actuator, is preferably coupled to the proximal end of the probe 42, for rotationally driving the probe 42 about its axis, and thereby rotating the sampling device 10. The rotation means 44 is preferably mounted to the carriage 37 and advances and retracts with the probe 42. The actuation means and rotation means can be controlled and monitored locally through a local controller/monitor 46, and/or controlled and monitored remotely through a remote controller/monitor 48.

The isolation system prevents fluid 20 from escaping from the pipe 22, while allowing advancement, retraction and rotation of the sampling device. In a preferred embodiment, an inner casing 50 extends through the flange 24 to permit passage of the probe 42 and attached sampling device 12 into the interior of the pipe 22. Purge lines (not shown) preferably communicate a pressurized inert purge gas, for example nitrogen, from an external source into the inner casing. First and second block-and-bleed valves 52, 54 are preferably provided, and in preferred form comprise pneumatically-driven remotely-actuated ball valves which are known in the art and are exemplified by the Marpac McCanna Model SS-FFP3-12-CC-4 6-in., oversize port, actuated, stainless-steel ball valve. As one skilled in the art will appreciate, the first block-and-bleed valve 52 is preferably coupled to the flange 24, for example by bolts, and the second block-and-bleed valve 54 is preferably coupled to the first block-and-bleed valve 52, for example, by bolts. An outer casing 56 is preferably coupled, as by bolting, to the second block-and-bleed valve 54. High-temperature, high-pressure gaskets or other sealing means can be provided at the bolted connections. Pressurization and venting means 58 can be provided to pressurize and vent the outer casing 56. A packing gland assembly 60 is attached to the outer casing 56, and forms a fluid-tight seal with the outer surface of the probe 42, permitting the probe to be advanced, retracted and rotated. In a presently preferred embodiment, the packing gland assembly comprises four sets of graphite-impregnated, split-ring, chevron packing rated for a pressure differential of 2000 psi (14 MPa). The length of the outer casing is preferably sufficient to accommodate the sampling device 12 between the packing gland assembly 60 and the second block-and-bleed valve 54 when the probe 42 is retracted and the second block-and-bleed valve 54 is closed.

When not sampling, the probe 42 can be fully retracted, both block-and-bleed valves 52, 54 closed, the packing gland assembly 60 removed, and a blind flange (not shown) installed onto the outer casing 56. The inner casing 50 can then be purged, the ball valve space of the block-and-bleed valves 52, 54 pressurized, and the outer casing 56 vented. In this manner, the pipe 22 or other vessel is sealed against the escape of fluid through the flange 24. Through the provision of releasable attachment means for connecting the control system and associated equipment to the support structure 30, such as, for example, releasable attachment means on the purge and vent connections to facilitate connection to the appropriate fittings in the desired facility, the sampling system 10 can be configured as a portable sampling system, adaptable for installation and use at any suitable flange or other access portal. For portability, the sampling system 10 can, for example, include a portable protective enclosure and may include purged junction boxes to facilitate explosion-proof electrical connections for use in areas where explosive gases may be present. Additionally, the sampling system 10 may, for example, be separated into a plurality of modular subsections mounted on skids (not shown) that can be releasably attached to each other for ease in transport, lifting, and installation of the portable sampling system. Alternatively, the control system and associated equipment can be permanently attached to the support structure 30, and thereby configured as a permanent sampling system.

Prior to beginning sampling, the block-and-bleed valves 52, 54 are verified to be closed, the outer casing 56 is vented to atmospheric pressure by the pressurization and vent means 58, the blind flange (not shown) removed, the probe 42 is installed within the outer casing 56, and the packing gland assembly 60 installed onto the outer casing 56. The outer casing 56 is pressurized, and the integrity of the packing gland assembly 60 can be tested for leakage as indicated by pressure loss within the outer casing 56. Pressures within the inner casing 50, the outer casing 56, and the ball valve space are equalized, and the block-and-bleed valves 52, 54 are opened. The sampling device 12 is then inserted through the sampling port 24, into the flow of fluid 20, by advancing the probe 42 via the actuation means. A stop 62 can be provided between the sampling device 12 and the sampling port 24 to prevent accidental over-insertion of the probe 42.

The sampling device 12 can be inserted into the flow of fluid 20 with its inlet port(s) facing downstream, whereby fluid flow does not initially enter the sampling device 12. After a predetermined warm-up period has elapsed, allowing the sampling device 12 to reach thermal equilibrium with the flowing fluid 20, the sampling device 12 can be rotated into the flow by the rotation means, so that its inlet port(s) face upstream into the oncoming flow of fluid 20 to initiate sampling. Sampling is conducted by extracting a portion of the fluid 20 from the pipe 22 or other vessel, and drawing the extracted portion into the particulate sampling means 14. Particulate matter entrained in the fluid 20 is collected, as will be described in greater detail below, by the particulate sampling means 14. The particulate-stripped fluid 20 may then be communicated from the particulate sampling means 14 to the alkali vapor collector 16, which collects alkali vapors from the fluid, as will be described in greater detail below. After passing through the alkali vapor collector 16, the extracted fluid is drawn through an internal passage or conduit 64 within the probe 42, passed through a heat exchanger 65, then passed through a condensate tank 66 for collection of any condensed liquid, and exhausted through an external exhaust system 68. The heat exchanger 65 is preferably water-cooled. The condensate tank 66 may be mounted to the carriage 39 to advance and retract with the probe 42. A flexible hose 70 preferably couples the condensate tank to the exhaust system 68.

Figure 28:
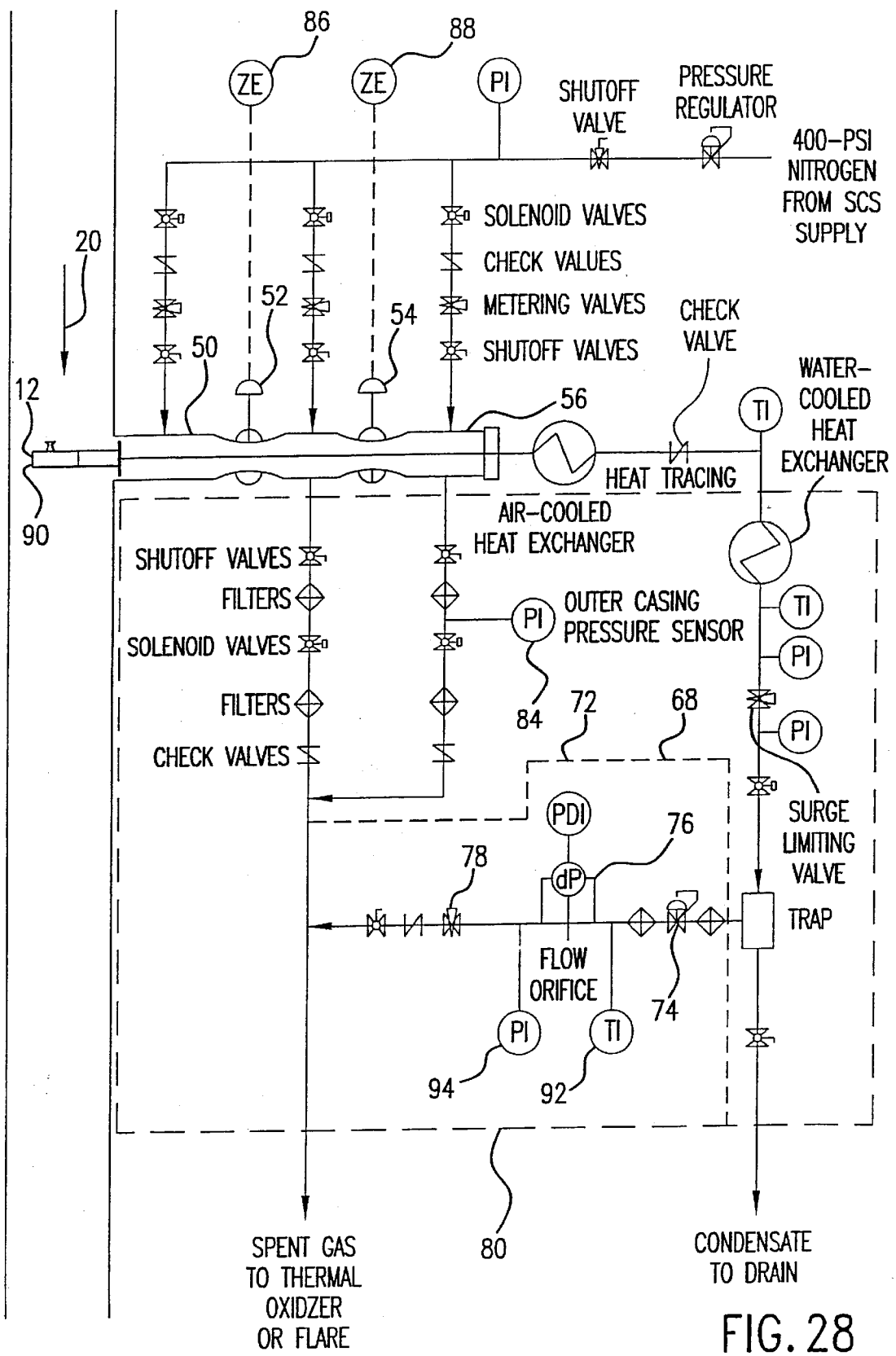
FIG. 28 shows a schematic of an example exhaust system according to a preferred form of the sampling system of the present invention.

Referring to FIGS. 1 and 28, the exhaust system 68 preferably comprises a flow control and metering system 72 comprising a pressure regulator 74, a calibrated flow orifice 76, and a flow control valve 78, which may for example be a manual flow control valve, and may, as one skilled in the art will appreciate, comprise filter, treatment, and/or recycle means (not shown). The flow control and metering system 72 is preferably enclosed in a heated sample flow control panel 80 to prevent condensation and to maintain a constant temperature at the flow orifice 76. As one skilled in the art will further appreciate, the flow orifice 76 may be periodically calibrated with a flow calibration standard, such as, for example, a laminar flow element (not shown) so that the sample gas flow can be reliably determined from the pressure drop across the flow orifice 76. Sampling is carried out isokinetically (i.e., at the same flow velocity as the flow of fluid 20 within the pipe 22 or other vessel), and in-situ (i.e., the particulate matter and the alkali vapors are collected while the sampling device 12 is within the pipe 22 or other vessel).

Since the sampling system 10 may be used in either oxidizing or reducing gas environments, the sampling device 12 and sampling probe 42 should be fabricated from an alloy suitable for use in either type of atmosphere. In addition to having suitable high-temperature strength characteristics, the selected alloy should be resistant to particle erosion, high-temperature corrosion, oxidation, carburization, and sulfidation. The preferred alloy is Haynes 556, Haynes HR-160, Rolled Alloys 333, or another alloy of similar composition. The preferred material of construction for all downstream components is Hastelloy C-276 or Hastelloy C-22, which is required to provide the necessary protection against chloride pitting corrosion. Stainless-steel alloys may be used in those downstream components of the sampling system 10 that are not exposed to process gas condensates, since the chloride content and low pH of the condensates can lead to severe chloride-pitting corrosion.

The selection of suitable materials for the gaskets or other sealing means is an important issue in the design of the sampling system 10, as the selection of the wrong materials may result in the loss of seals between the various sampling system 10 components. For example, a Kaowool 2000 gasket, which contains an organic binder for increased structural integrity, may be used as a gasket in the sampling system. However, to minimize the potential for sample contamination due to possible burning of the organic binder, it is preferred that a structurally stable gasket without an organic binder be used in the system. For example, a Carborundum 972H gasket, which is made of a binder-free ceramic paper may be utilized.

As noted above, the insertion and retraction of the sampling device 12 via the probe 42 is controlled by the local controller/monitor 46 or by the remote controller/monitor 48. The controller 46, 48 is operatively connected to a plurality of automatic interlocks to avoid unsafe operating conditions. The plurality of automatic interlocks may preferably include a pressure switch 84 connected to the outer casing 56, a first position switch 86 attached to the first block-and-bleed valve 52, a second position switch 88 attached to the second block and bleed valve 54, and a thermocouple 90 attached to the sampling device 12 (the thermocouple 90 preferably runs from the sampling device 12 thru the probe 42 and exits the back end of the probe 42 into operative communication with the controller 46, 48). The controller 46, 48 does not allow the operator to begin an insertion sequence unless the pressure switch 84 indicates that the outer casing 56 is pressurized with an inert gas, such as nitrogen, and there is no leakage. When this condition is met, the controller 82 will open the block-and-bleed valves 52, 54. Movement of the probe 42 is not allowed until the position switches 86, 88 indicate that the block-and-bleed valves 52, 54 are fully open. The controller 46, 48 then gradually moves the sampling device 12 via the probe 42 through the block-and-bleed valves 52, 54 and into the process gas stream 20. The rate of insertion is controlled to avoid heating the sampling device 12 too rapidly.

Upon insertion of the sampling device 12 into the gas stream 20, the sampling device 12 begins to heat up. When the thermocouple 90 on the sampling device 12 indicates that the sampling device 12 is fully heated, the controller 46, 48 rotates the particulate sampling means 14 into the gas flow 20 and opens the flow control valve 78 to begin sampling. The flow control valve 78 is preferably manually adjusted to provide the desired sampling rate as indicated by the flow orifice 76. However, it is contemplated that the controller 46, 48 may automatically adjust the flow control valve 78. The sampling flow rate is set to achieve isokinetic sampling and is not adjusted during the sampling run, because a change in the sampling rate during the run would cause a change in the cut points of the cyclone subassemblies and impactor stages, making it impossible to accurately determine the size distribution of the particulate sample. The thermocouple 90 on the sampling device senses the temperature at which the sample is collected which is communicated to the controller 46, 48. Additional sensors may communicate with the controller, for example a first pressure sensor, such as a transducer, may sense and communicate the pressure proximate to piping near the outer casing. A temperature sensor 92 and a second pressure sensor 94 may be operatively coupled to the exhaust system 68 proximate the flow measurement orifice 76 so that the sample gas volumes and particulate loadings can be corrected to process conditions and to standard conditions.

After the preset duration of sampling, the controller 46, 48 closes the flow control valve 76 and rotates the sampling means 14 out of the gas flow 20. The flow rate of purge gas is then increased, and the probe 42 is withdrawn to bring the sampling device 12 into the inner casing 50 for cooling. The controller 46, 48 does not allow any further retraction of the probe 42 until the temperature of the sampling device 12, as sensed by the thermocouple 90 and communicated to the controller 46, 48, is well below the operating limit of the block-and-bleed valves 52, 54. After the sampling device 12 has cooled sufficiently, the probe 42 is withdrawn further to draw the sampling device 12 into the outer casing 56, and the block-and-bleed valves 52, 54 are closed. The controller 46, 48 checks the actuation means to ensure that the probe 42 is fully retracted before the block-and-bleed valves 52, 54 are closed. The outer casing 56 is then purged with inert gas and depressurized so that the sampling means 14 can be recovered.

Cyclone Sampler

The present invention also provides an improved cyclone sampler 100, which will be described with particular reference to preferred embodiments depicted in FIGS. 3–13. The cyclone sampler 100 can comprise the particulate sampling means 14 of the sampling system 10 described above, or may find application in a variety of other particulate sampling applications. According to a preferred form of the invention, the cyclone sampler 100 generally comprises a manifold 102, and at least one cyclone subassembly. A plurality of cyclone subassemblies of different sizes are preferably provided, each adapted to collect particulate matter within a particular range of particle sizes. The plurality of cyclone subassemblies act to separate the incoming dust sample into an equal plurality number of separate particle-size fractions. As one skilled in the art will observe, if the backup filter is included, one additional particle-size fraction will be separated onto the backup filter. In the presently preferred embodiment depicted in the figures, five cyclone subassemblies 104, 106, 108, 110, and 112 are provided. It will be understood by those skilled in the art, however, that more or less than five cyclone subassemblies can be provided. The mean particle sizes of the five particle-size fractions of the preferred embodiment are nominally in the range of 0.5 to 15 microns. Those skilled in the art will understand that these particle-size fractions can be altered by changing the design and/or dimensions of the individual cyclones subassembly.

Referring to FIGS. 7–13, the manifold 102 releasably engages each cyclone subassembly 104, 106, 108, 110, 112 within a corresponding cyclone receptacle 114, 116, 118, 120, 122, respectively. Sacrificial connection means such as, for example, a C-ring which may be used in combination with a bracket system are preferably provided for removably retaining each cyclone subassembly within its respective receptacle. The preferred C-ring is a common metallic seal, known in the art, and serves the same purpose as a nonmetallic gasket in sealing the mating surface of each cyclone subassembly to the corresponding mating surface in each cyclone receptacle. The preferred C-ring is exemplified by the Advanced Products Co. Type ECE (external-pressure) C-rings or equivalent fabricated from Waspalloy alloy with a 2–3 mil nickel coating, which are suitable for use at temperatures up to 1600° F. The bracket system holds the cyclone subassemblies in the cyclone receptacles and adequately compresses the C-ring to ensure that there is no leakage between the cyclone subassemblies and the cyclone receptacles.

Figure 10A:
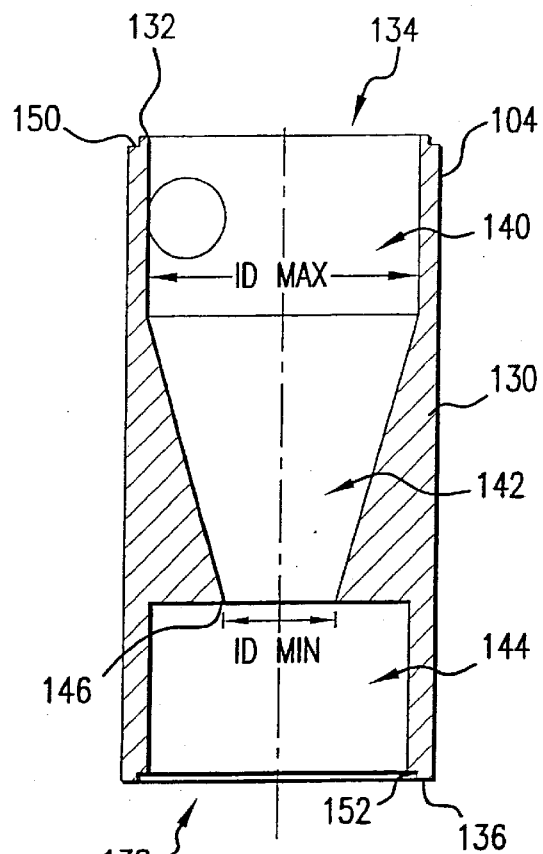
FIGS. 10A and 10B show a cyclone subassembly.
Figure 10B:
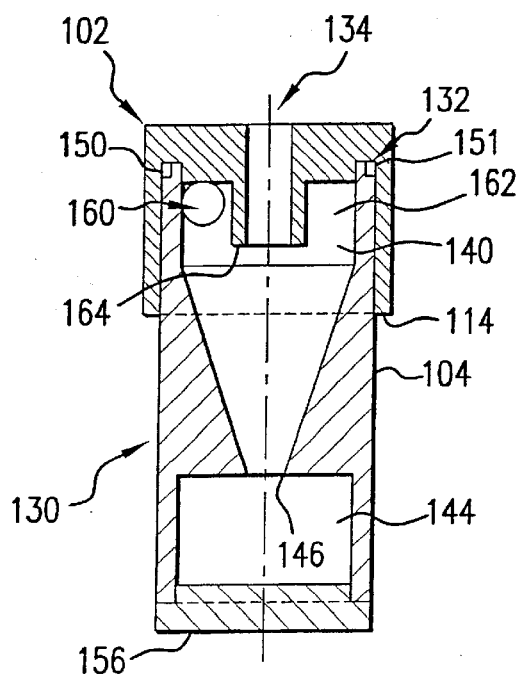
Figure 11A:
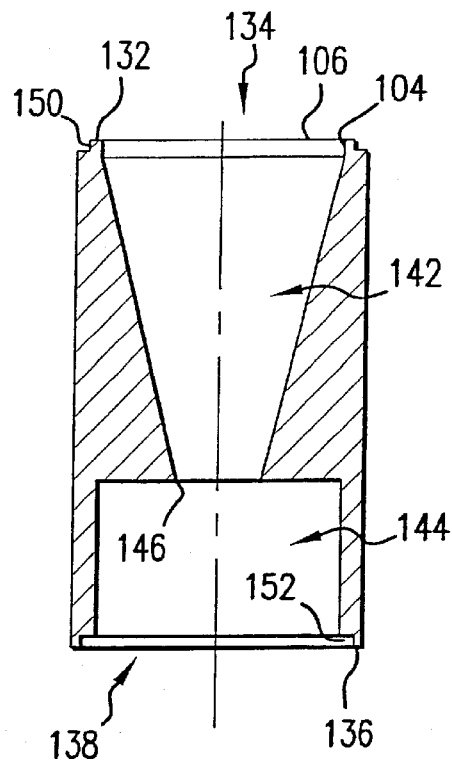
FIGS. 11A and 11B show a cyclone subassembly.
Figure 11B:
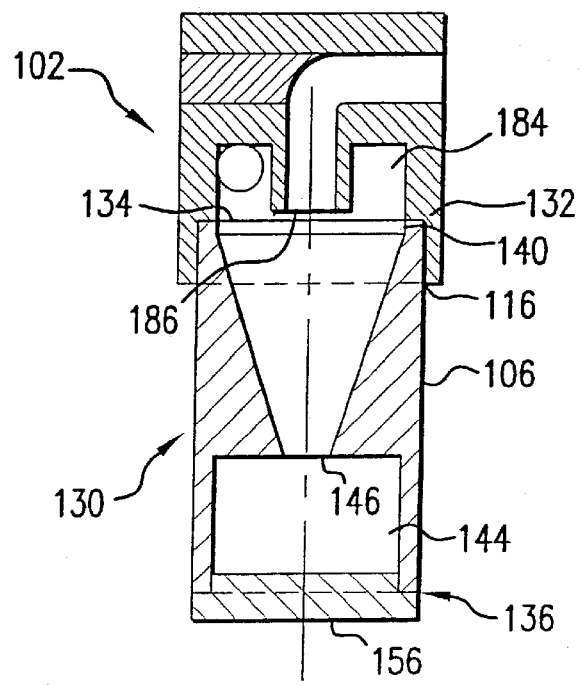
Figure 12:
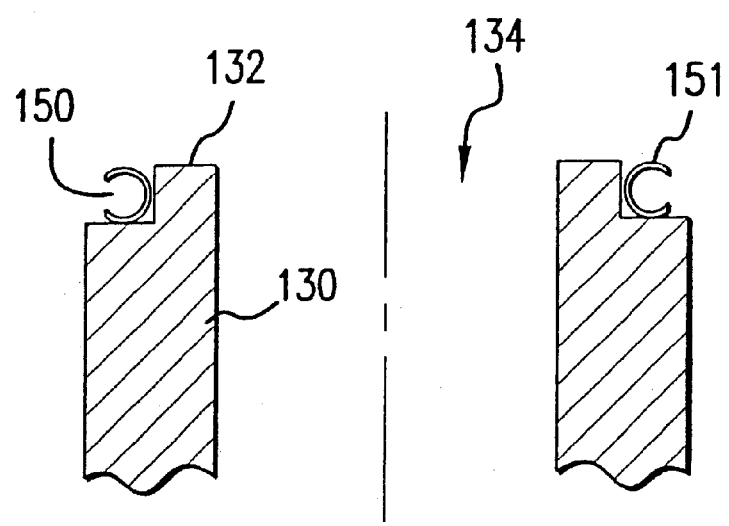
FIG. 12 shows a detail of a connector portion of the cyclone subassembly.
Figure 13:
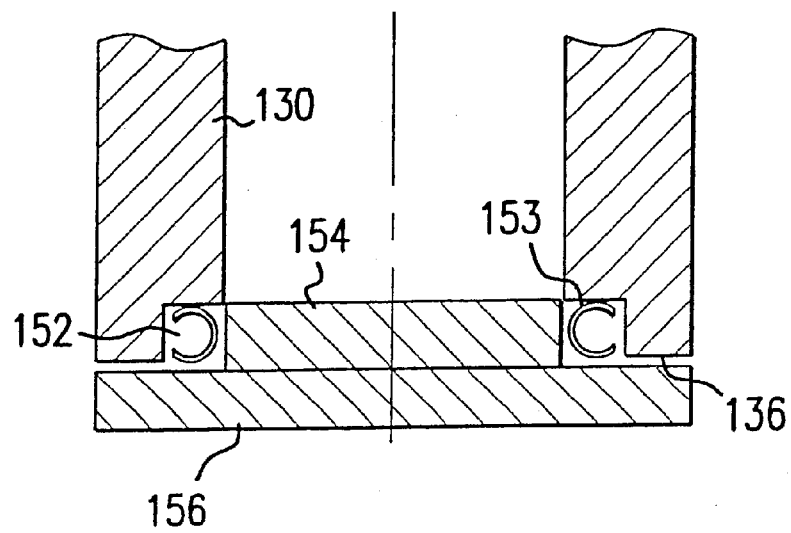
FIG. 13 shows a detail of a cap retainer portion of the cyclone subassembly.

FIGS. 10A–13 show representative examples of individual cyclone subassemblies and detailed views of portions thereof, according to preferred forms of the present invention. FIGS. 10A and 10B, for example, depicts a preferred embodiment of the first cyclone subassembly 104, and FIGS. 11A and 11B depicts a preferred embodiment of the second cyclone subassembly 106. The general structure of the third, fourth and fifth cyclone subassemblies 108, 110, 112 is preferably substantially similar to the second cyclone subassembly 106, except for sizing differences demonstrated by way of example in Table 1 below. In general, and as described with reference to FIGS. 10A–13, the cyclone subassemblies 104–112 each comprise a generally cylindrical outer body housing 130, having a first end 132 defining an entry port 134, and a second end 136 defining an access opening 138. Each cyclone subassembly further comprises an internal bore or chamber comprising a generally straight-walled lead-in section 140 adjacent the entry port, a collection cup 144 adjacent the access opening 138, and a generally conical cyclone chamber 142 between the lead-in section 140 and the collection cup 144. The walls of the lead-in section 140 are preferably configured to generally match a corresponding portion of the respective cyclone receptacle 114–122. The walls of the cyclone chamber 142 slope inwardly from a maximum inner diameter $ID_{max}$ adjacent the lead-in section 140 to a minimum inner diameter $ID_{min}$ adjacent the collection cup 144. The collection cup 144 is preferably a straight-walled, generally cylindrical chamber having an inner diameter greater than the minimum inner diameter of the cyclone chamber 142, thereby forming an angled lip 146 between the cyclone chamber 142 and the collection cup 144, which assists in retaining collected particulate matter in the collection cup 144. The first end 132 of the cyclone subassembly preferably comprises an outer circumferential groove 150 or other surface feature for retaining a C-ring 151 or other sacrificial connector for engaging a cooperating portion of the respective cyclone receptacle of the manifold 102. The second end 136 of cyclone subassembly preferably comprises an inner circumferential groove 152 or other surface feature for retaining a C-ring 153 or other sacrificial connector for engaging a cooperating projection 154 of a cap 156 for closing the access opening 138 to retain collected particulate matter within the collection cup 144 until the cap 156 is removed for sample analysis.

TABLE 1

Example Cyclone Subassemblies

| Cyclone Subassembly | Collected Particle Size Range (microns) | $ID_{max}$ (inches) | $ID_{min}$ (inches) | ID of Cup (inches) | Overall Length (inches) |
|---|---|---|---|---|---|
| 1 | 8 to 15 and larger | 1.763 | 0.743 | 1.678 | 4.141 |
| 2 | 5 to 8 | 1.443 | 0.512 | 1.443 | 2.912 |
| 3 | 2 to 5 | 1.226 | 0.301 | 1.250 | 2.358 |
| 4 | 1 to 2 | 1.003 | 0.201 | 0.850 | 1.966 |
| 5 | 0.4 to 1 | 0.603 | 0.331 | 0.603 | 1.560 |

The overall length is from the top of the tapered section of the cyclone subassembly to the bottom of the collection cup 144, which corresponds to the distance between the first end 132 of the cyclone subassembly and the projection 154 of the cap 156 (i.e., the distance between where tapered section of the cyclone subassembly seals against the cyclone receptacle and where cap 156 seals against the collection cup 144). Those skilled in the art will recognize that the above dimensions can be altered to change the particle-size fractions collected in each individual cyclone subassembly.

Figure 7:
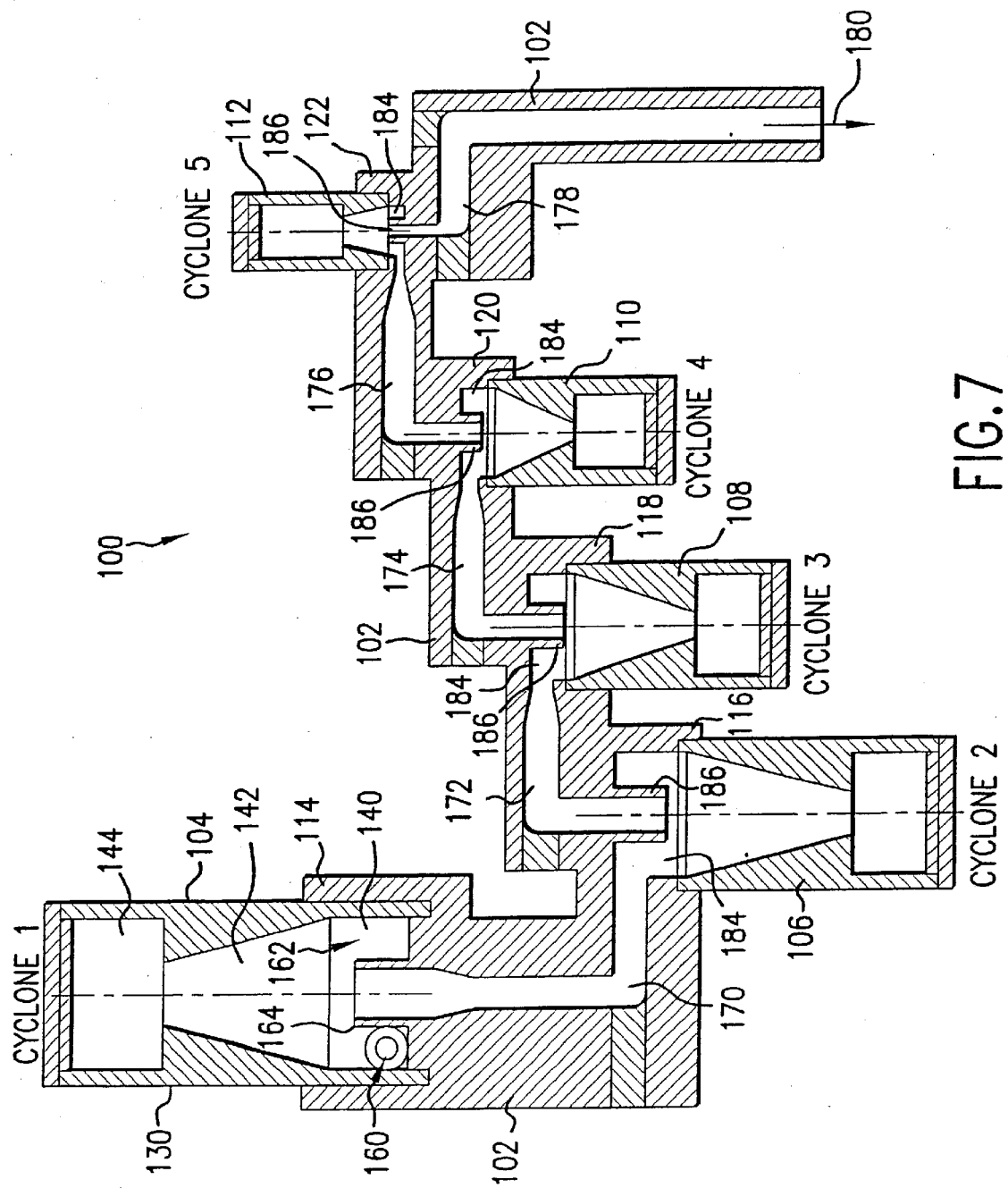
FIG. 7 is a schematic diagram showing an example of a conceptual flow path through the cyclone assembly and manifold layout of a cyclone sampler of the present invention.
Figure 8:
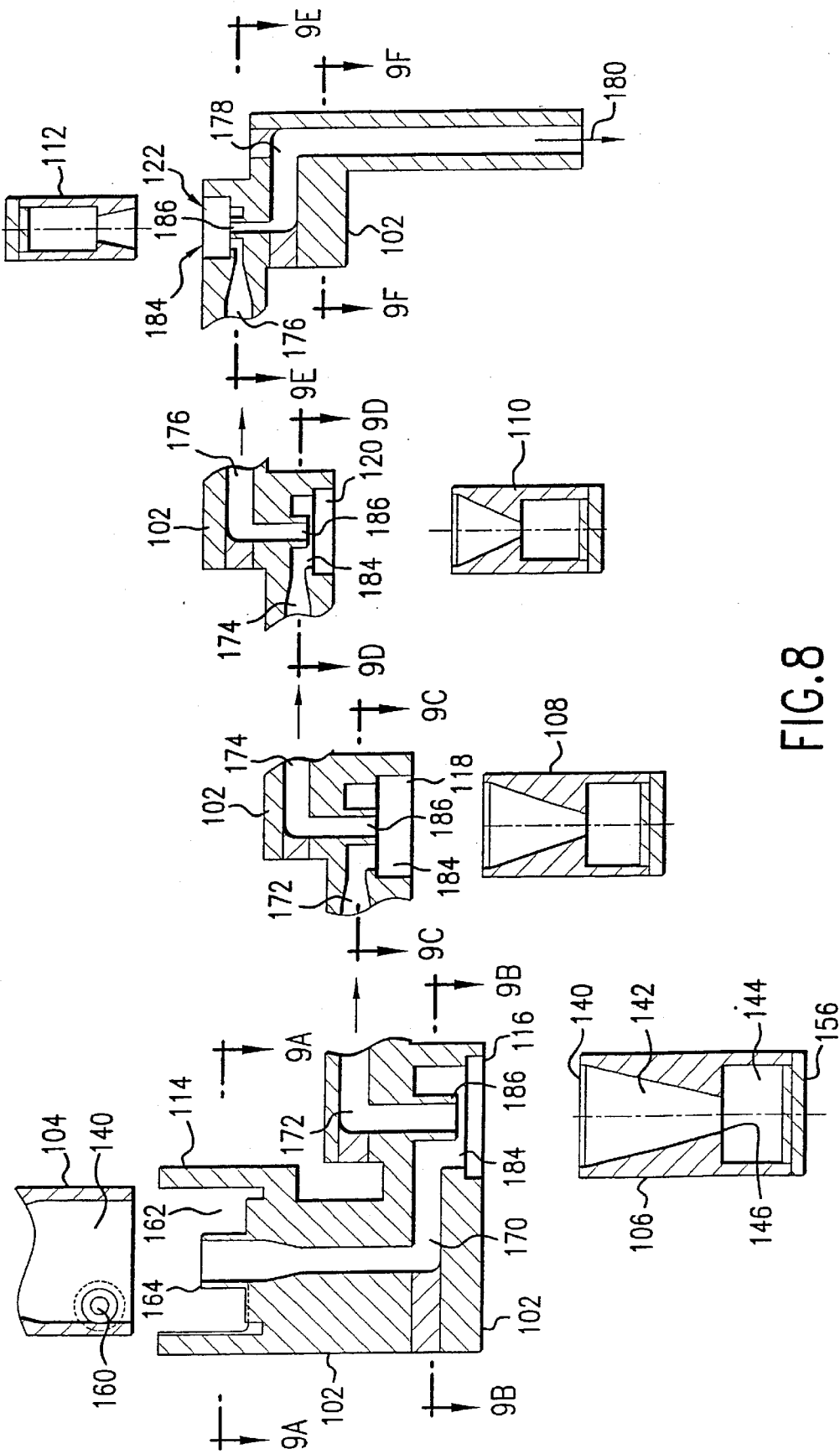
FIG. 8 is a schematic exploded view of the example shown in FIG. 7.
Figure 9A:
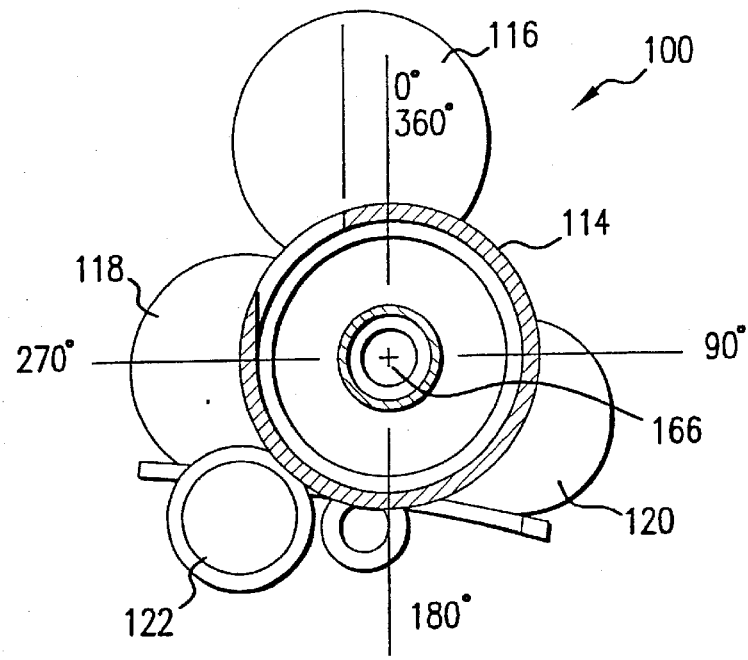
FIGS. 9A–9F show cross-sectional views of the cyclone manifold taken along the respective designation lines shown in FIG. 8.
Figure 9B:
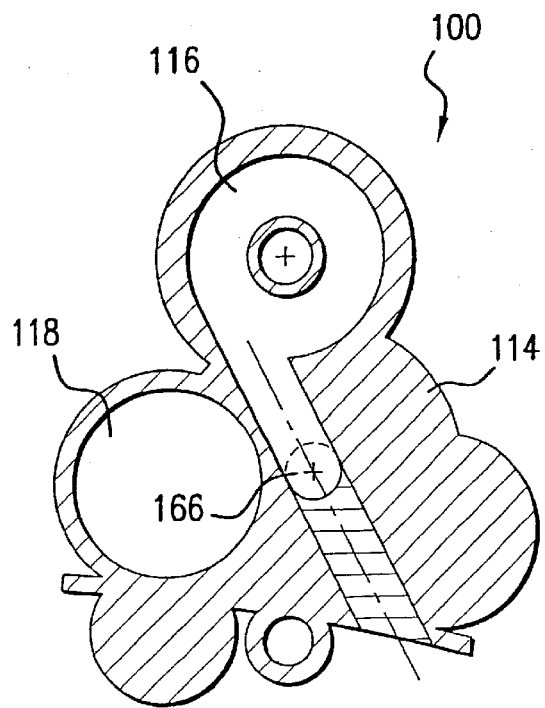
Figure 9C:
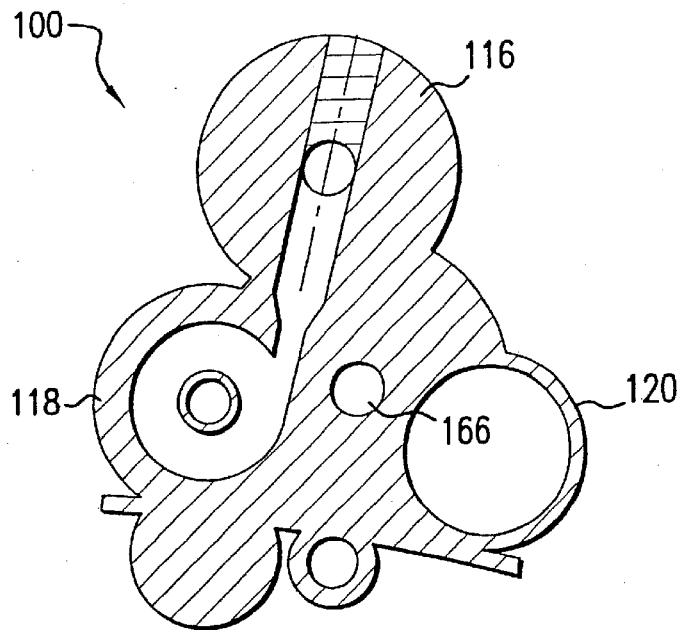
Figure 9D:
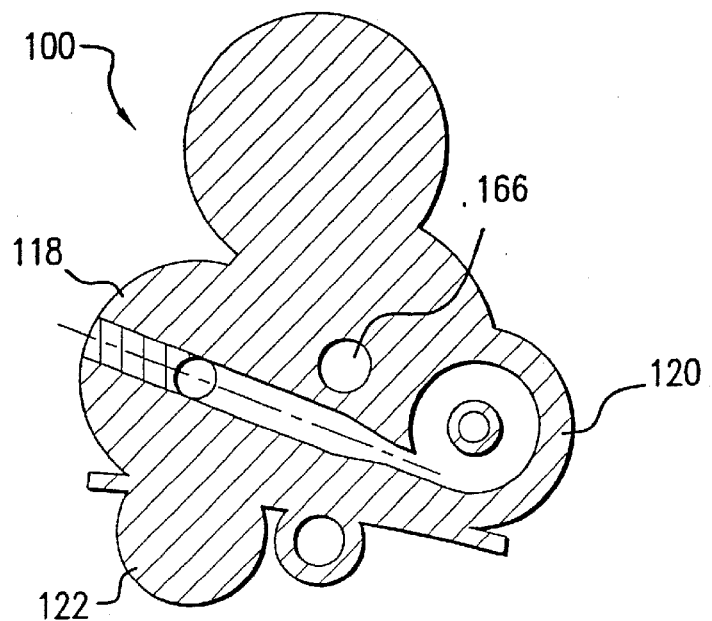
Figure 9E:
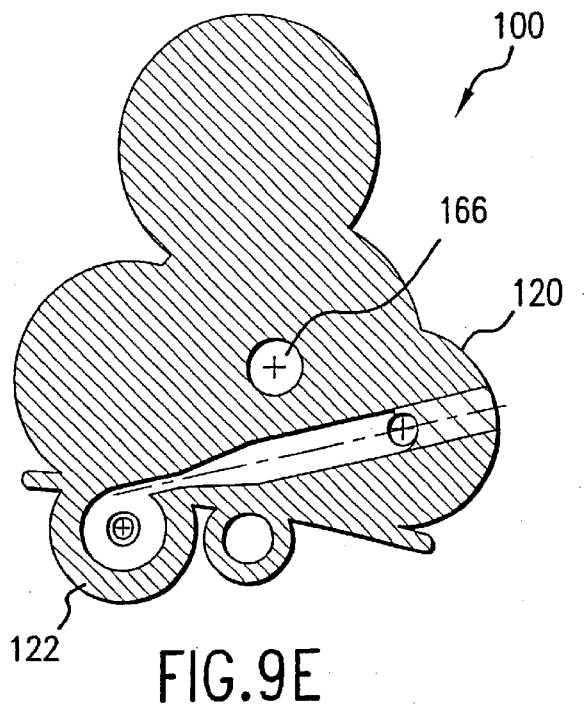
Figure 9F:
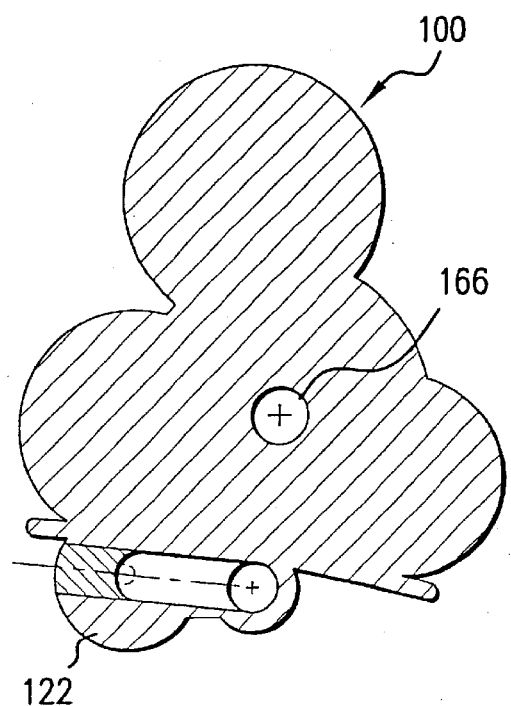

To assist in the understanding of the communication of extracted particulate-laden fluid samples through the cyclone sampler 100, FIGS. 7 and 8 schematically illustrate an example of the layout of the cyclone assemblies 104–112 and the flowpaths through the manifold 102. FIGS. 7 and 8 are not intended to portray the actual structural arrangement of the manifold 102 or the cyclone subassemblies. With particular reference to FIG. 7, the extracted sample fluid enters the cyclone sampler 100 isokinetically through a main inlet nozzle 160, adjacent the first cyclone subassembly 104. The sampled fluid enters through the body housing 130 of the first cyclone subassembly 104 and generally tangential to the inner wall thereof. An annular inlet section 162 is formed between the inner wall of the lead-in section 140 of the first cyclone subassembly 104 and a duct 164 projecting outwardly from the manifold 102, generally centrally within the first cyclone receptacle 114.

Particulate matter of a predetermined size range (see Table 1 above), which is entrained in the sample fluid entering the first cyclone subassembly 104, traverses a "cyclone-shaped" path, from the main inlet nozzle 160, through the lead-in section 140 and the cyclone chamber 142, into the collection cup 144. Particulate matter not within the predetermined size range for collection in the first cyclone assembly 104 remains entrained in the fluid, exits through the duct 164, and is communicated through a first conduit 170 in the manifold to the second cyclone subassembly 106. In similar fashion, fluid and entrained particulate matter are communicated from the second cyclone subassembly 106 to the third cyclone subassembly 108 through a second conduit 172, from the third cyclone subassembly 108 to the fourth cyclone subassembly 110 through a third conduit 174, and from the fourth cyclone subassembly 110 to the fifth cyclone subassembly 112 through a fourth conduit 176. An exit conduit 178 communicates particulate-stripped fluid from the fifth cyclone subassembly 112 to a discharge 180 of the cyclone sampler 100. The discharge 180 can be communicated to the conduit 64 of the probe 42, or can be passed to additional sampling means as detailed below.

Example dimensions of the manifold conduits are provided in Table 2 below:

be minimized. In this manner, the sampler 100 can be better adapted for in-situ sample extraction from confined vessels than conventional cyclone samplers. As seen best with reference to the preferred embodiment depicted in FIGS. 9A–9F, the angular offset of the cyclone receptacles 114–122 can be described with reference to a clockwise coordinate system about the longitudinal axis 166 extending concentrically with the central axis of the first cyclone receptacle 114, with 0° defined toward the top of the FIGS. 9A–9F, 90° defined toward the right of the FIGS. 9A–9F, 180° defined toward the bottom of the FIGS. 9A–9F, 270° defined toward the left of the FIGS. 9A–9F, and 360° defined again toward the top of the FIGS. 9A–9F. Defined in this manner, the second cyclone receptacle 116 is offset at approximately 350°, the third cyclone receptacle 118 is offset at approximately 270°, the fourth cyclone receptacle 120 is offset at approximately 115°, and the fifth cyclone receptacle 122 is offset at approximately 225°.

Figure 3:
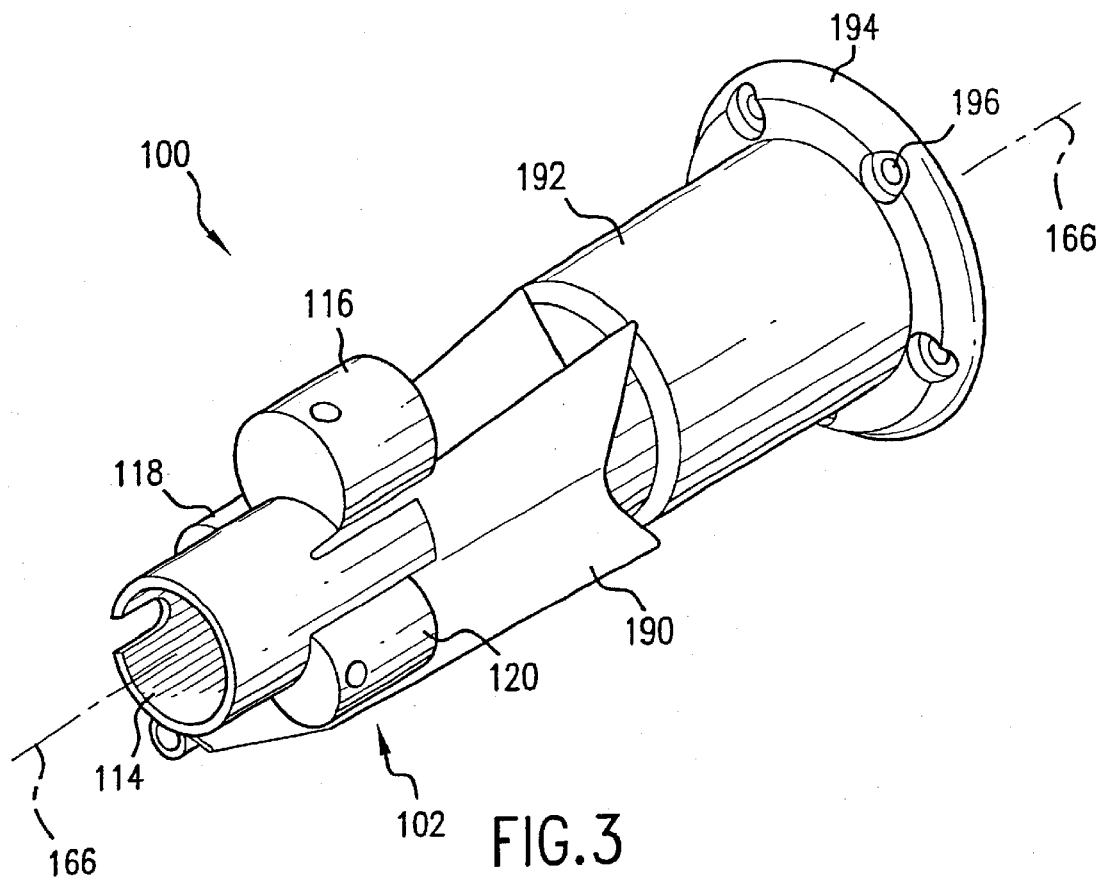
FIG. 3 shows a perspective view of a cyclone manifold of a cyclone sampler.
Figure 4:
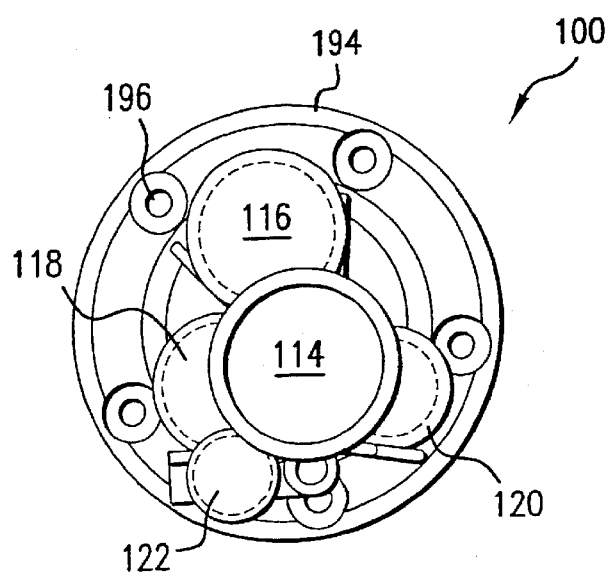
FIG. 4 is an end elevational view of the cyclone manifold of FIG. 3.
Figure 5:
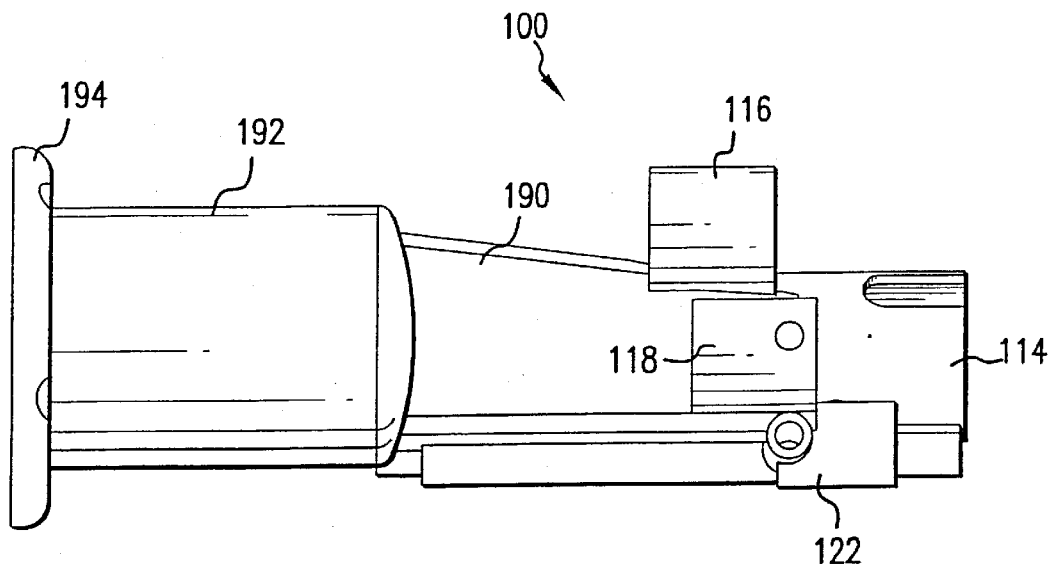
FIG. 5 is a first side elevational view of the cyclone manifold of FIG. 3.
Figure 6:
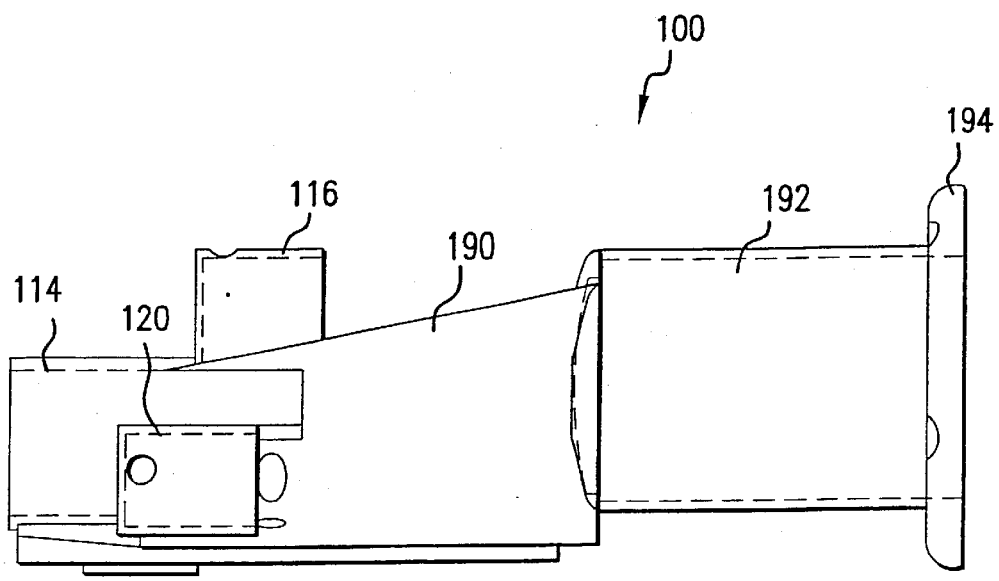
FIG. 6 is a second side elevational view of the cyclone manifold of FIG. 3.

Longitudinal placement of the individual cyclone subassemblies are determined by the placement of the receptacles in the cast manifold 102. This is best defined using the distance between the mounting flange 194 and the far end of each cyclone receptacle (114, 116, 118, 120, and 122) as illustrated in FIGS. 3, 5, and 6. Example dimensions of the relative longitudinal placement distances are provided in Table 3 below:

TABLE 3

Example Longitudinal Placement Distance Dimensions

| Receptacle/Cyclone No. | Approx. Distance from flange to far end, inches. |
| --- | --- |
| 1 | 13 ± 0.010 |
| 2 | 10 ± 0.010 |
| 3 | 11 ± 0.010 |
| 4 | 11.5 ± 0.010 |
| 5 | 12 ± 0.010 |

Referring to FIGS. 10A–11B, the second through fifth cyclone subassemblies 106, 108, 110, 112 have relatively

TABLE 2

Example Manifold Dimensions

| Interconnecting tube conduit | Interconnecting points | $ID_{max}$ (at inlet to cyclone body/swirl section, inches.) | $ID_{min}$ (at entrance of interconnecting tube, inches) | Overall length (from centerline to tangent point on cyclone wall, inches) |
| --- | --- | --- | --- | --- |
| Main Inlet Nozzle | process gas stream to 1st Cyclone | 0.500 ± 0.003 | 0.250 ± 0.003 | 2.125 ± 0.003 |
| 1st Conduit | Cyclone 1 to Cyclone 2 | 0.590 ± 0.003 | 0.397 ± 0.003 | 1.932 ± 0.003 |
| 2nd Conduit | Cyclone 2 to Cyclone 3 | 0.414 ± 0.003 | 0.295 ± 0.003 | 2.070 ± 0.003 |
| 3rd Conduit | Cyclone 3 to Cyclone 4 | 0.328 ± 0.003 | 0.201 ± 0.003 | 1.920 ± 0.003 |
| 4th Conduit | Cyclone 4 to Cyclone 5 | 0.234 ± 0.003 | 0.120 ± 0.003 | 2.144 ± 0.003 |
| Exit Conduit | Cyclone 5 to Backup filter | 0.375 ± 0.003 | 0.375 ± 0.003 | 7.000 ± 0.003 |

By arranging the cylone receptacles in an angularly offset pattern around the circumference of the manifold 102, about a longitudinal axis 166, and longitudinally offset from one another, as shown in FIGS. 3–6 and 9A–9F, the length of the sampler 100 in the axial direction (along the axis 166) can shorter lead in sections 140 than the first cyclone subassembly 104. Thus, rather than forming an annular inlet section 162 in the manner described above with reference to the first cyclone assembly 104, an annular chamber 184 surrounding a duct 186 is formed in the manifold adjacent the respective second through fifth cyclone receptacles 116, 118, 120, 122. It will be understood by those skilled in the art that the manner of providing an annular inlet section, as described with reference to the first cyclone subassembly 104, is readily interchangeable with the manner of providing an annular chamber, as described with reference to the second through fourth cyclone subassemblies, and either can be provided to any or all cyclone subassembly stages of the cyclone sampler 100 as a matter of design choice.

As seen best with reference to FIGS. 3–6, the cyclone sampler 100 can optionally be combined with an alkali vapor collector 16, which will be described in greater detail below, to form the sampling device 12. In a preferred embodiment, the manifold 102 of the cyclone sampler 100 is attached to or integral with one or more support brackets 190, which are in turn attached to or integral with a housing portion 192 of the alkali vapor collector 16. The housing portion 192 of the alkali vapor collector 16 can comprise mounting means, such as a mounting flange 194 provided with bolt holes 196, for attachment to the probe 42. In this embodiment, the discharge 180 from the cyclone sampler 100 is communicated to an inlet of the alkali vapor collector 16, alkali vapors are collected from the fluid in the alkali vapor collector 16, and the discharge from the alkali collector is communicated to the conduit 64 of the probe 42.

To match the thermal expansion characteristics of the cyclone manifold 102, it is preferred that the individual cyclone subassemblies be fabricated from the same alloy used in casting the manifold 102 (for example, Haynes 556, Haynes HR-160, Rolled Alloys 333, or equivalent materials).

Cascade Impactor

The present invention also provides an improved cascade impactor 240, which will be described with particular reference to preferred embodiments depicted in FIGS. 14–24. The cascade impactor 240 can comprise the particulate sampling means 14 of the sampling system 10 described above, or may find application in a variety of other particular sampling applications. According to a preferred form of the invention, the cascade impactor 240 generally comprises a housing 242 comprising a precollector portion 244 and an impactor shell 246. The precollector portion 244 preferably comprises an entry nozzle 248, shown in detail in FIG. 23, for isokinetically extracting a portion of fluid 250 containing particulate matter from a process gas or other fluid. The cascade impactor 240 is particularly adapted for in-situ sampling within a fluid.

The entry nozzle 248 communicates fluid 250 to a plenum 252 within the precollector portion 244, which in turn, communicates fluid to a duct 254 leading into an interior chamber 255 within the impactor shell 246. The sampled fluid 250 is communicated from the duct 254, through a diverging nozzle transition 256, to a fluid distribution stage 258. The transition 256 is a generally cylindrical element adapted to be received within the interior chamber 255 of the impactor shell 246. The transition 256 has a first end 260 adapted to abut an end wall of the interior chamber 255, and a second end 262 adapted to engage the distribution stage 258. The first end 260 can be provided with a reduced outer diameter for centering the transition 256 within the interior chamber 255, and the second end can be provided with a groove or lip for engaging a cooperating surface of the distribution stage 258. A temperature-impervious gasket 264, such as a compressed ceramic fiber gasket or other sealing means, can be provided between an end wall of the interior chamber 255 and the transition 256. A generally conical diverging nozzle 266 is provided to communicate fluid 250 through the transition 256. The nozzle 266 expands in the direction of fluid flow through the transition 256, from a minimum inlet diameter at the first end 260 to a maximum outlet diameter at the second end 262. The fluid distribution stage 258 preferably comprises a disc-shaped element having a central diffuser plate 268 surrounded by one or more annular slots 268. The slots 270 are preferably angled inwardly in the direction of fluid flow and allow communication of fluid 250 through the fluid distribution stage 258.

At least one, and preferably a plurality of particle collection stages 280 are provided in the interior chamber 255 of the impactor shell 246. For example, fluid 250 is distributed from the fluid distribution stage 258 over and through each particle collection stage 280A–F, in sequence. Particulate matter is collected at each particle collection stage 280A–F, to be segregated into desired ranges of particle size. Each particle collection stage 280 preferably comprises a jet plate 282 and a corresponding collection substrate 284, each of which will be described with reference to preferred forms in greater detail below.

Typically, particle mass segregation is accomplished in a cascade impactor by directing fluid flow through a series of jet plates, each jet plate having an array of jet openings provided therethrough. The jet plates restrict fluid flow, and the fluid is accelerated through the jet openings. The size and number of jet openings in a particular jet plate will determine the flow velocity of the fluid and entrained particles passing therethrough. Because all of the particles entrained in the fluid travel at approximately the same flow velocity v, particles of different masses m within a fluid flow will have different kinetic energies, as the following equation illustrates: $KE=1/2\ mv^2$. At each stage of a typical cascade impactor, the fluid and entrained particles accelerated through the jet openings are directed toward a collection substrate associated with the jet plate. Particles exceeding a threshold kinetic energy will impact with the collection substrate and become lodged on or in the surface thereof. In some instances, the surface may be coated or treated to prevent particle rebound. Lower mass particles not meeting the threshold kinetic energy required to impact and lodge with the collection substrate are deflected by fluid flow across the collection substrate, and remain entrained in the fluid and continue on to the next stage.

Successive stages of a typical cascade impactor are provided with progressively smaller jet openings, resulting in increasing fluid flow velocity—and thus increasing particle kinetic energy—at each successive stage. In this manner, progressively lighter particles become lodged in or on the collection substrates of each successive stage. After sampling, the collection stages can be then removed and analyzed, as by weighing, to determine characteristics such as the particle size distribution and total particulate loading of the particulate matter in the fluid.

The cascade impactor 240 of the present invention provides a number of improvements over previously-known cascade impactors. For example, the present invention provides alignment means for aligning the jet plates 282 and collection substrates 284 of at least one particle collection stage 280. In preferred form, the alignment means comprises a stage retainer cup 290 and cooperating projections on the jet plates 282 and the collection substrates 284. Alternatively, the alignment means can comprise any cooperating surface features, such as projections, recesses, slots, component shapes or tabs, having a first surface feature or features provided on the jet plates 282 and the collection substrates 284, and a cooperating second surface feature or features provided on the stage retainer cup 290.

Alternatively, the stage retainer cup 290 can be omitted, and the alignment means can comprise any cooperating surface features, having a first surface feature or features provided on the jet plates 282 and the collection substrates 284, and a cooperating second surface feature or features provided on the interior chamber 255 of the impactor shell 246.

Figure 21:
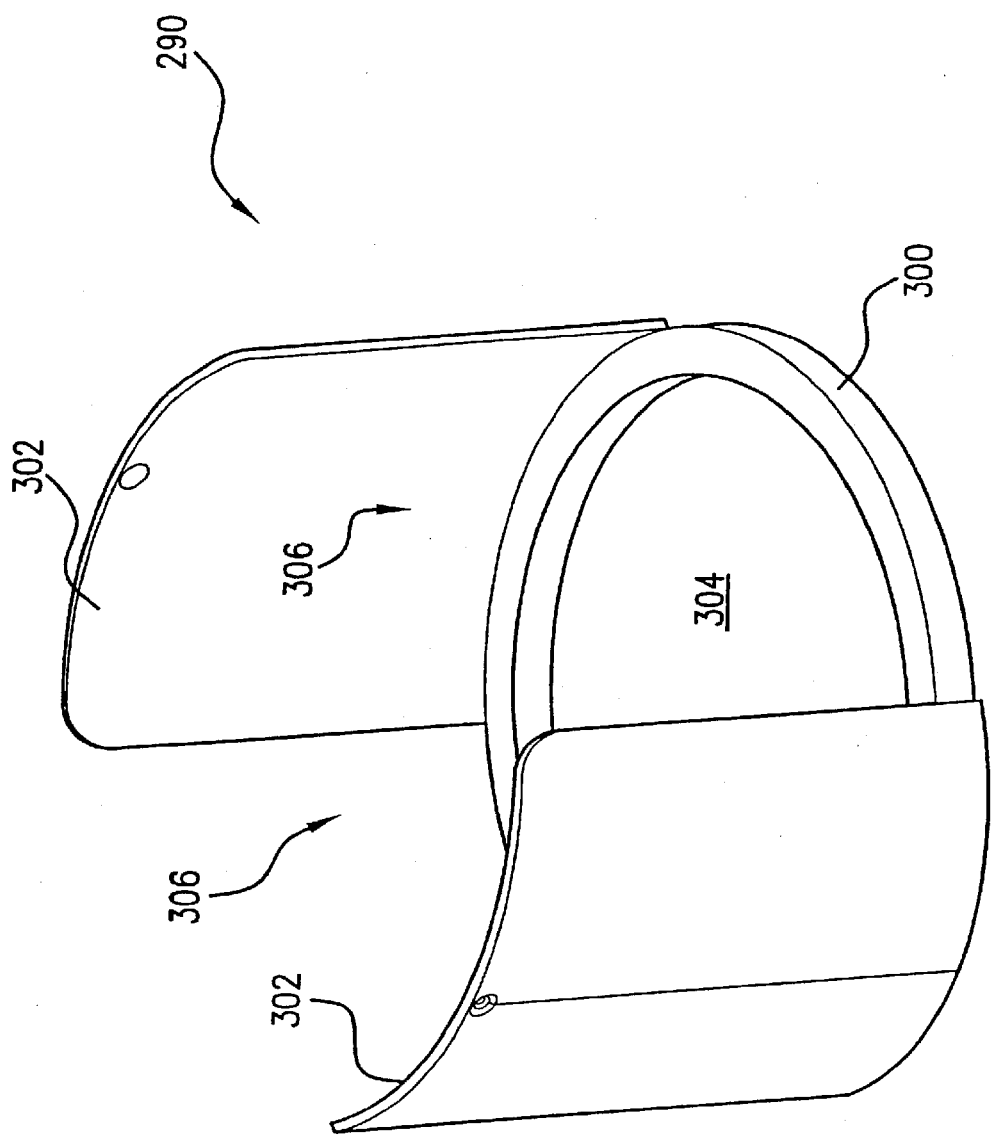
FIG. 21 shows a perspective view of an alignment component of the cascade impactor.
Figure 22:
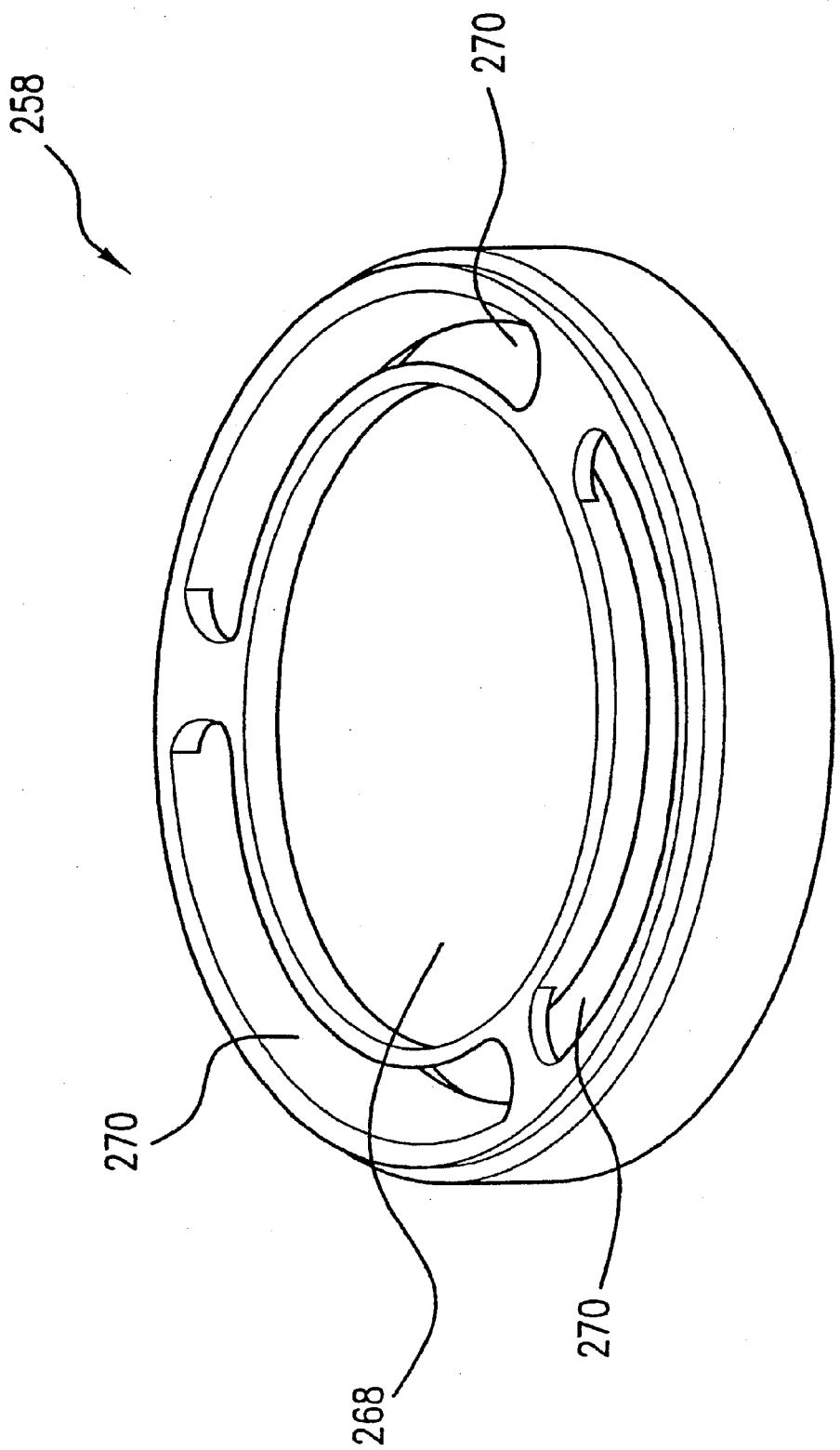
FIG. 22 shows a perspective view of a fluid flow distribution stage of the cascade impactor.
Figure 23:
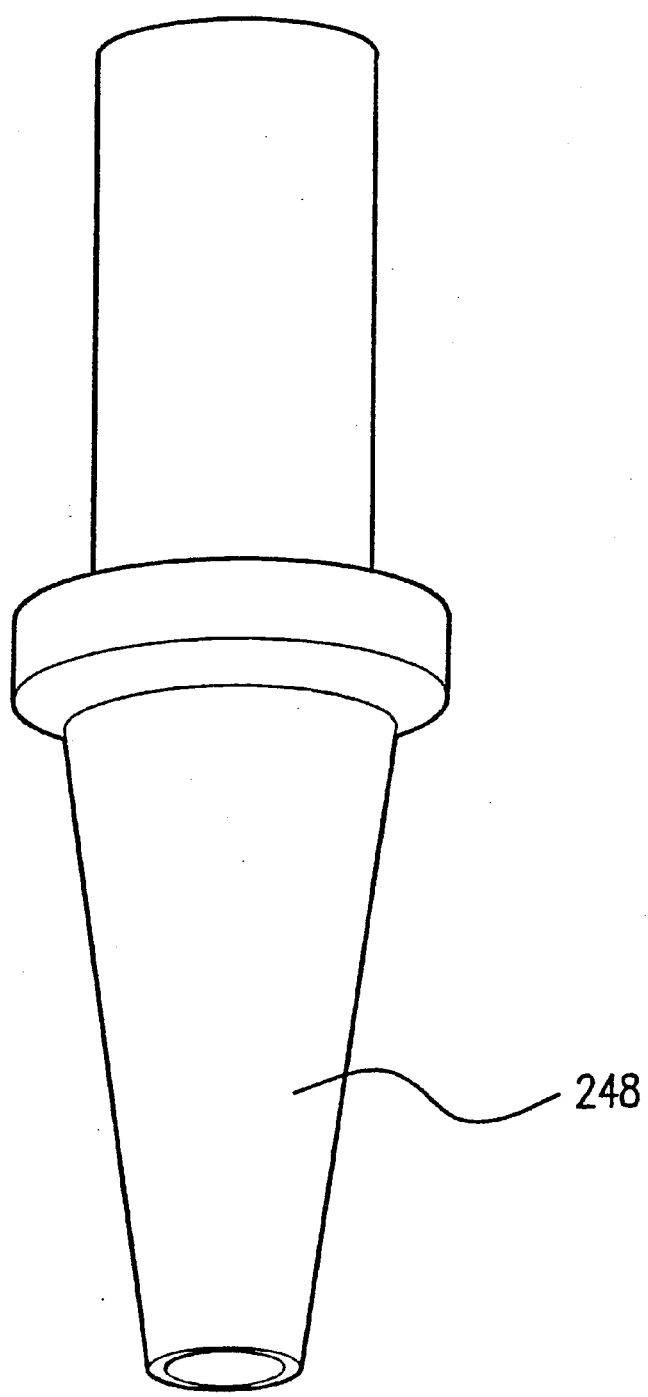
FIG. 23 shows a schematic view of an entry nozzle component of the cascade impactor.
Figure 24:
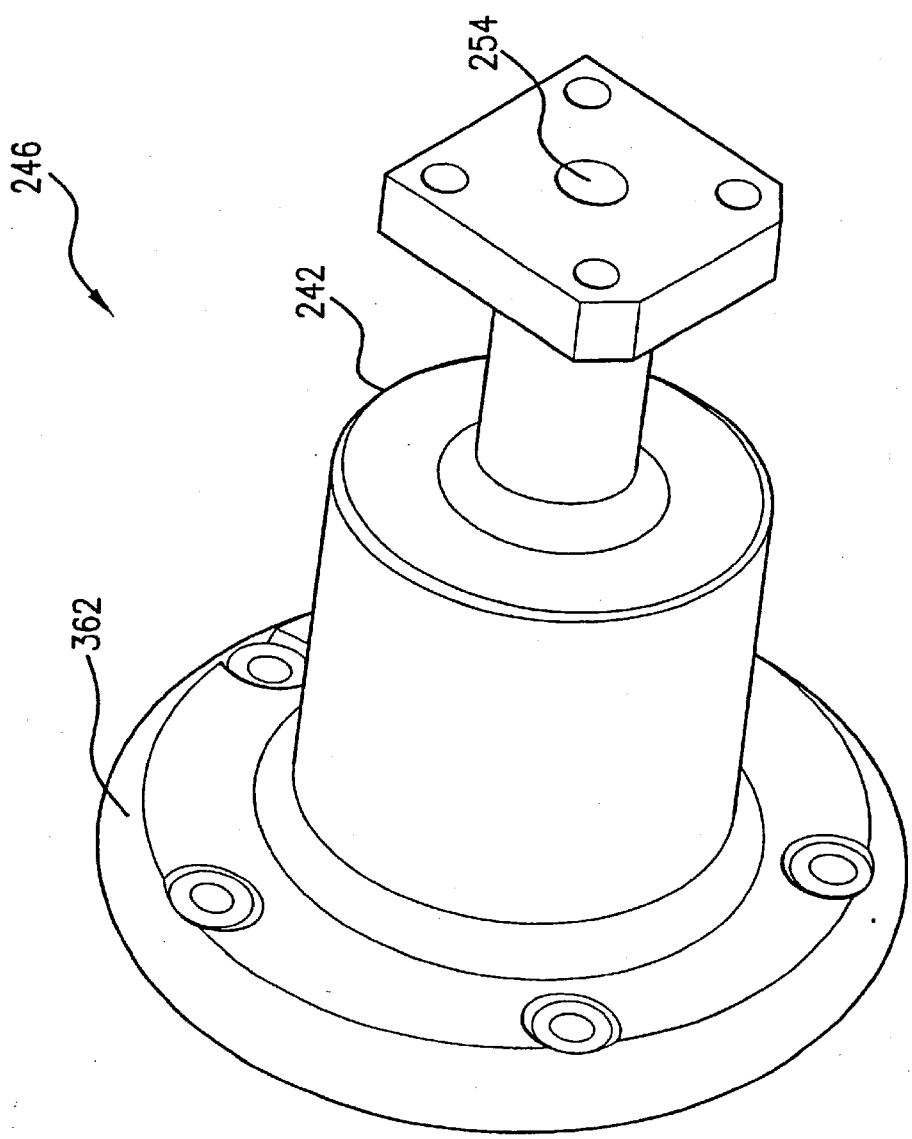
FIG. 24 shows a perspective view of a shell component of the cascade impactor.

The stage retainer cup 290 is shown in detail according to a preferred embodiment in FIG. 21. The cup 290 generally comprises a ring-shaped base 300, and one or more upright collar portions 302. The base 300 preferably includes a generally circular central opening 304. In the depicted embodiment, two diametrically opposed collar portions 302 are provided, each extending generally perpendicularly upward from the base 300, and each generally curved to match the radius of curvature of the ring-shaped base 300. Each collar portion 302 preferably spans approximately or slightly less than 90° of the circumference of the base 300. In this manner, two diametrically opposed circumferential gaps 306 are formed between the two collar portions 302, each gap 306 preferably spanning approximately or slightly more than 90° of the circumference of the base 300. The stage retainer cup 290 is generally sized and shaped to fit within the interior chamber 255 of the impactor shell 246, with sufficient clearance to permit easy insertion and removal.

Figure 15B:
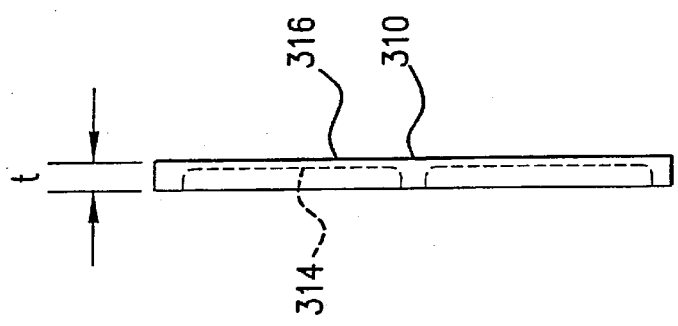
FIGS. 15A and 15B show plan and side views, respectively, of a jet plate blank according to a preferred form of the present invention.
Figure 15A:
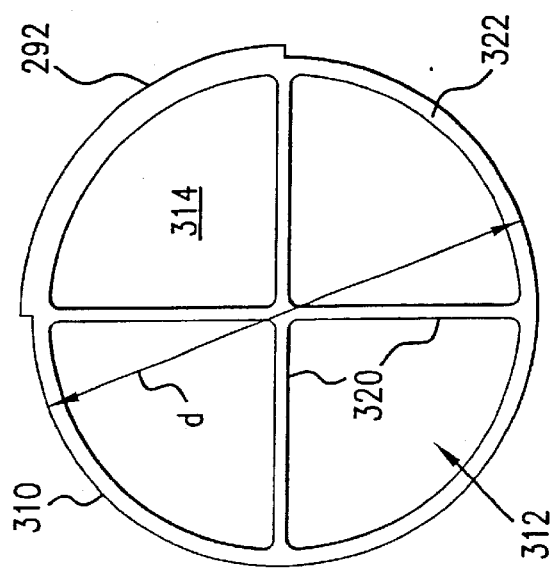

FIGS. 15A and 15B depict a blank 310 for forming jet plates 282 according to preferred forms of the present invention. The blank 310 preferably includes a generally cylindrical body portion 312 having a first surface 314, a second surface 316, a diameter d and a thickness t. The blank 310 preferably further comprises a radially outward projection 292 adapted to engage the stage retainer cup 290 or other alignment means. The projection 292 preferably spans approximately or slightly less than 90° of the circumference of the blank 310, thereby allowing the projection to be removably engaged within a gap 306 between collars 302 of the stage retainer cup 290. The blank 310 is preferably machined or otherwise formed to include one or more integral spacers extending from and projecting outwardly from the first surface 314 of the body portion 312. The integral spacers can take the form of one or more diametrical ribs 320, and/or a circumferential lip 322. The embodiment depicted in FIGS. 15A and 15B include first and second diametrical ribs 320, arranged at right angles to one another, and a circumferential lip 322. In alternative embodiments, the integral spacer can take the form of any outward projection or protrusion formed into or provided on the jet plate 282.

Figure 16:
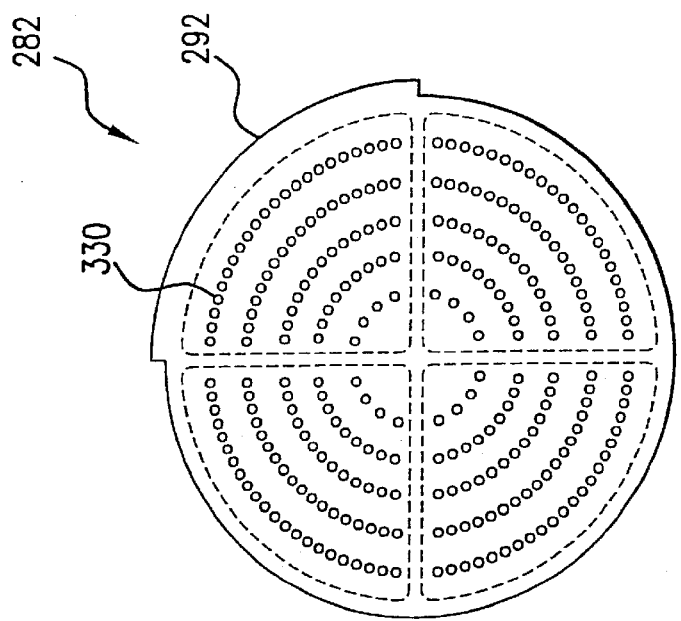
FIG. 16 shows a plan view of a first embodiment of the jet plate.
Figure 18:
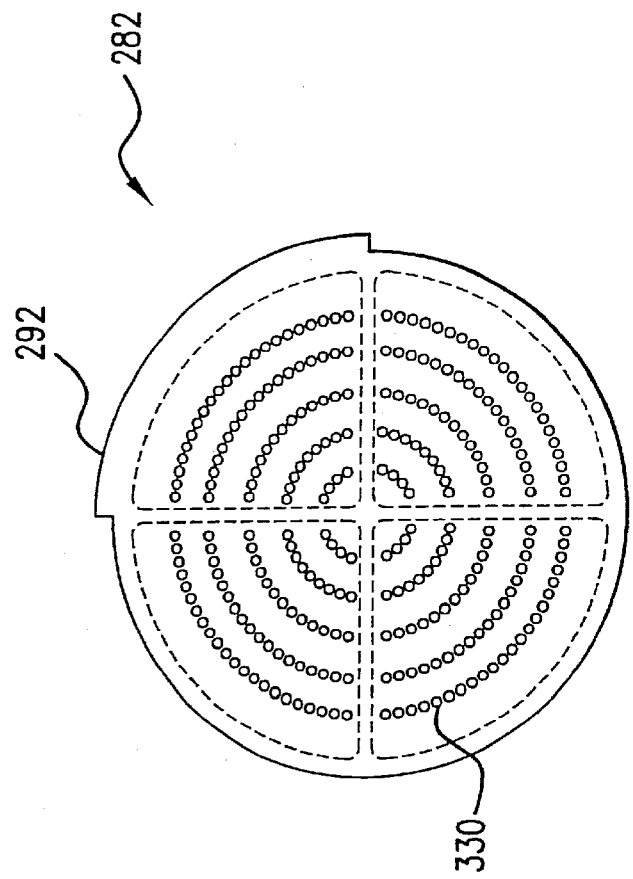
FIG. 18 shows a plan view of a third embodiment of the jet plate.
Figure 17:
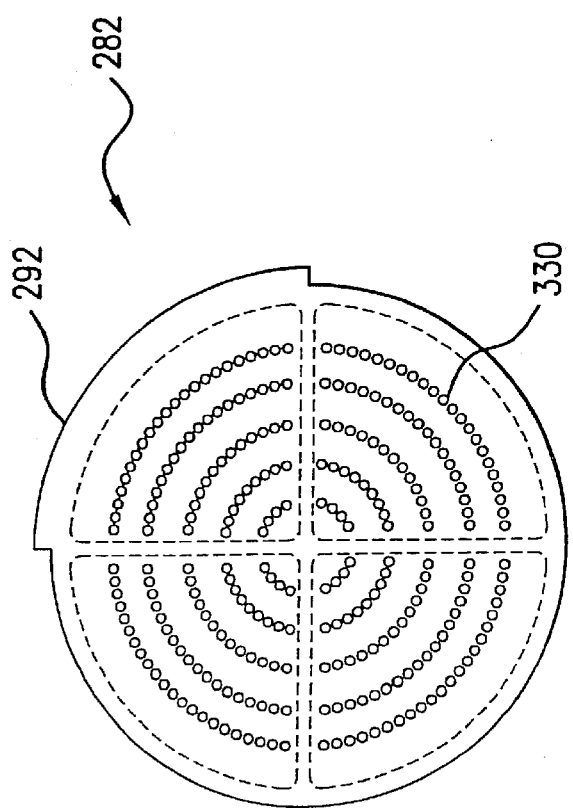
FIG. 17 shows a plan view of a second embodiment of the jet plate.

FIGS. 16–18 show different embodiments of jet plates 282 that can be fabricated from blanks 310 substantially as described above. A plurality of jet holes 330 are formed extending through each jet plate 282, forming a portion of a flowpath through the impactor 240. In a presently preferred embodiment, each jet plate 282 is provided with a number of generally circular arrays of jet holes 330, arranged at radially-spaced intervals along the body portion 312. Five circular arrays of jet holes 330 are provided on each of the jet plates 282 depicted in FIGS. 16–18. Each circular array can be segregated into four quadrants, corresponding to arc segments extending between adjacent diametrical ribs 320. The layout and spacing of the jet holes 330 on the jet plate 282, and the size and diameter of the jet holes 330 will vary between jet plates of different stages. One or more filter stages 332 can be provided downstream in the fluid flowpath from the particulate collection stages 280. Additionally, one or more blank stages 334 may be provided downstream of the filter stages 332. Example dimensions of several presently preferred embodiments of jet plates are disclosed in Table 4 below.

TABLE 4

Example Jet Plate Details

Figure 14:
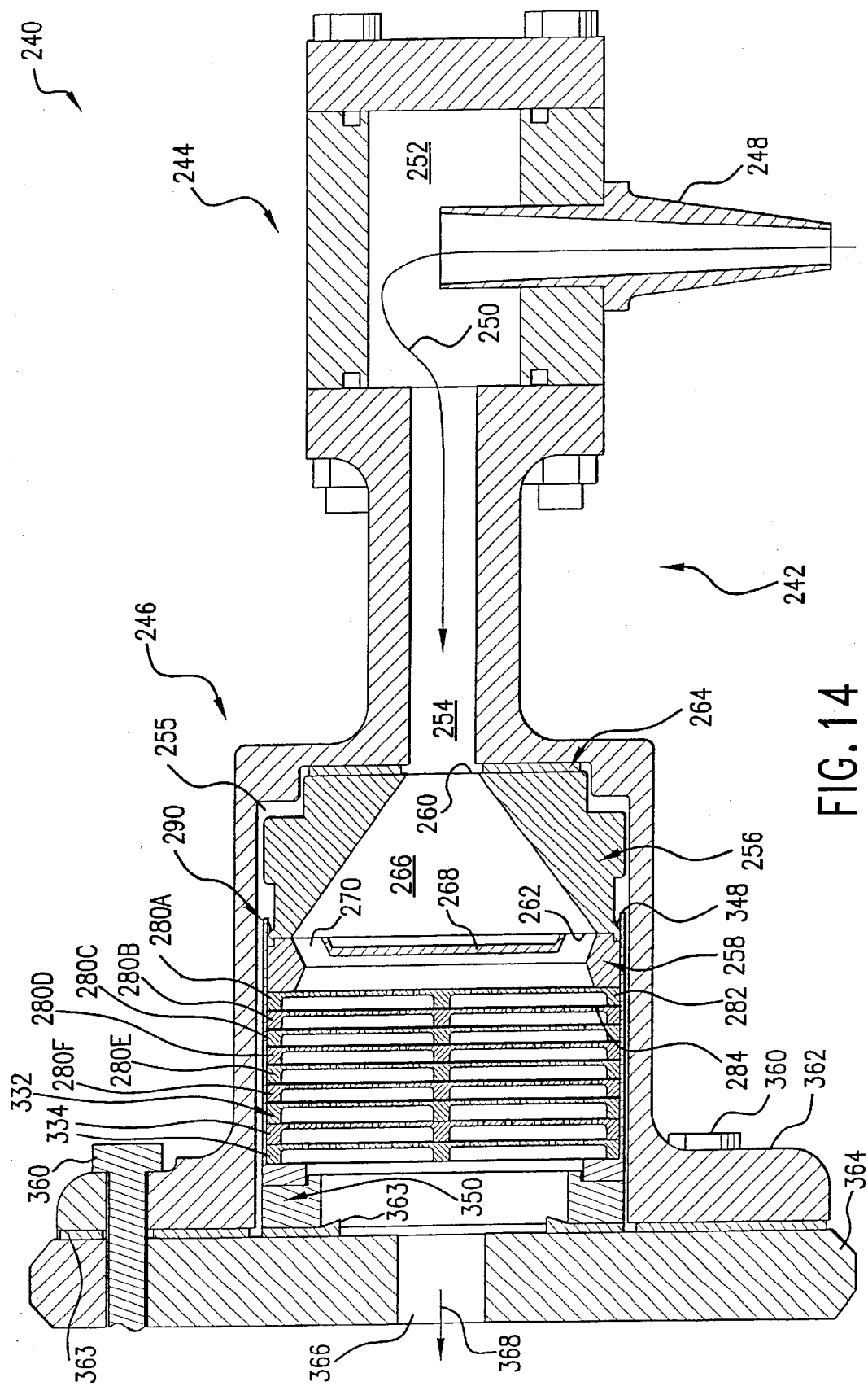
FIG. 14 shows a cross-sectional view of a cascade impactor according to a preferred form of the present invention.

| Jet Plate (282) No. | Exemplary structure | Total No. of Jet Holes | Jet Diam. (in.) | Plate Thickness (in.) | Spacing between plates (in.) |
|---|---|---|---|---|---|
| 1 | Ref. FIG. 16 | 264 | 0.0299 | 0.0375 | 0.100 |
| 2 | Ref. FIG. 14 | 264 | 0.0210 | 0.0255 | 0.100 |
| 3 | Ref. FIG. 16 | 264 | 0.0135 | 0.0175 | 0.100 |
| 4 | Ref. FIG. 14 | 264 | 0.0100 | 0.0175 | 0.100 |
| 5 | Ref FIG. 16 | 156 | 0.0100 | 0.0175 | 0.100 |
| 6 | Ref. FIG. 14 | 264 | 0.0373 | 0.0375 | 0.100 |
| filter stage plate | Ref. FIG. 14 | 264 | 0.0645 | 0.0375 | 0.100 |
| blank stage plate | Ref. FIG. 14 | 264 | 0.0645 | 0.0375 | 0.100 |

The circular arrays of jet holes 330 of any two adjacent jet plates 282 are perferably radially staggered, as seen by a comparison of FIGS. 16 and 18, thereby forming a serpentine or zig-zag flowpath for fluid passing through the jet holes 330 of successive stages 280 of the impactor 240. Referring to Table 4 above and the FIGS. 16–18, the size of the jet holes 330 in successive downstream jet plates will preferably incrementally decrease to ensure that higher and higher velocities are achieved downstream so that smaller and smaller particles within the gas stream may be appropriately separated as the gas passes downstream through the various stages. Therefore, referring to the jet plates 282 described in Table 4 above, one example of the orientation of the jet plates 282 forming the successive particulate collection stages 280 of the impactor 240 would have jet plate No. 2 placed downstream and adjacent jet plate No. 1. If desired to continue the serpentine flow path for the fluid, jet plate No. 3 can be placed downstream and adjacent jet plate No. 2, and as one skilled in the art would appreciate, jet plate No. 4 could be placed downstream and adjacent jet plate No. 3, jet plate No. 5 could be placed downstream and adjacent jet plate No. 4, and jet plate No. 6 could be placed downstream and adjacent jet plate No. 5. This orientation provides both the desired incremental increase in gas stream velocity and forms the desired serpentine flowpath for the fluid through the cascade impactor. The filter stage(s) 332 and the blank stage(s) 334 may be placed downstream of the particulate collection stages 280 if desired.

Each particulate collection stage 280 preferably further comprises a collection substrate 284, shown according to preferred forms in FIGS. 19 and 20. Each collection substrate 284 preferably comprises a metal sheet or foil, having a size and shape generally matching that of the jet plate blank 310, with a generally circular body portion 340 and an outward projection 342, preferably spanning approximately or slightly less than 90° of the circumference of the body portion 340. Each collection substrate 284 preferably further comprises at least one passage therethrough, preferably in the form of one or more slots 344, and at least one impact surface 346. In the depicted embodiments, five slots 344 and interposed impact surfaces 346 are segregated into quadrants by four webs 348, thereby forming a slot pattern of twenty slot segments. As one skilled in the art will appreciate, when the projections 292 of the jet plates 282 and the projections 342 of the collection substrates 284 are installed within a gap 306 of the stage retainer cup 290, the webs 348 of the collection substrates 284 align with the diametrical ribs 320 of the jet plates 282, and the arrays of jet holes 330 of each jet plate 282 align with impact surfaces 346 of the corresponding collection substrate 284. Because the hole patterns of jet plates 282 of adjacent stages are radially staggered, the slot patterns of the corresponding collection substrates 284 of adjacent stages are also radially staggered, as seen by a comparison of FIGS. 19 and 20. Example radial positions R1–R5 of slots 344 and slot thicknesses for presently preferred embodiments of collection substrates are disclosed in Table 5 below.

TABLE 5

Example Collection Substrate Details

| Attached jet plate No. (Ref Chart 4 for jet plate No) | Slot Thickness | Exemplary structure | R1 (in.) | R2 (in.) | R3 (in.) | R4 (in.) | R5 (in.) |
|---|---|---|---|---|---|---|---|
| 1, 3, 5, Blank | 0.070 | Ref. FIG. 17 | 0.325 | 0.513 | 0.700 | 0.900 | 1.088 |
| 2, 4 | 0.070 | Ref. FIG. 18 | 0.225 | 0.425 | 0.600 | 0.790 | 0.985 |

Referring to FIG. 14, the cascade impactor 240 is preferably assembled by inserting any blank stages 334, filter stages 332, jet plates 282, and collection substrates 284 in the stage retainer cup 290, with the respective projections 292, 342 engaged within one of the gaps 306 between collar portions 302 of the cup 290. The proper alignment of the various components is thereby ensured and maintained. The fluid distribution stage 258 and the transition 256 can also be engaged by the stage retainer cup 290. A retaining lug 348 or other retaining means can be provided on the stage retainer cup 290 for releasably retaining the components in this assembled configuration. This assembly is then inserted into the interior chamber 255 of the impactor shell 246. An annular spacer or retainer 350 can then be placed in the interior chamber 255 to retain the assembly in position. The housing 242 containing the assembled components as described above can be attached, preferably via releasable attachment means such as bolts 360 engaging a mounting flange portion 362 of the housing 242, to a support plate 364 or other support means. One or more temperature-impervious gaskets 363 can be provided between the mounting flange 362 and the support plate 364. A passage 366 through the support plate 364 communicates the discharge 368 from the cascade impactor. The support plate 364 can, for example, comprise a portion of the probe 42 for insertion and retraction into a process fluid 20, and the discharge 368 can be communicated from the cascade impactor 240 to the conduit 64 of the probe 42.

Sample fluid 250 thus traverses a flowpath through the cascade impactor 240. The fluid 250 and entrained particulate matter enters the cascade impactor 240 through the entry nozzle 248, passes through the plenum 252 and the duct 254, expands through the diverging nozzle 266 of the transition 256, and is distributed for introduction to the particle collection stages 280 by the fluid distribution stage 258. The flowpath passes through the jet holes 330 of the jet plates 282, and particulate matter is impacted and collected on the collection substrates 284, segregated according to particle mass. The fluid 250 then passes through any filter stages 332 provided downstream in the flow path, passes through any blank stages 334 provided, passes through the opening of the spacer 350, and is discharged from the cascade impactor.

Experience with the use of cascade impactors at high temperatures and pressures suggests that there is a significant problem with particle bounce and reentrainment caused by excessive jet momentum at these conditions. To address this problem, the impactor design described herein has large numbers of small holes to minimize the momentum of the impactor jets. The lower stages are similar to those used in commercial Andersen impactors. A new precollector portion 244 and fluid distribution stage 258 have been provided to collect large particles.

The preferred materials for fabrication of the impactor shell 246, precollector portion 244, and jet plates 282 are Haynes 556, HR-160, or RA333. Extensive testing has been done to establish the optimum materials for the collection substrates 284, since these materials must experience minimal weight change when exposed to the process gas at operating temperatures. In other words, the material must not oxidize or adsorb or react with any species in the gas phase, since such an interaction would cause an artificial weight change, which would invalidate the measurement of collected particulate mass. Various thin metal foils were evaluated. The following metal foils were tested: 310 stainless steel, 310 stainless steel modified with tantalum, 316 stainless steel, Havar, Haynes 230, Inconel 600, several different formulations of iron aluminide, and various chromized and aluminized forms of these alloys. The thicknesses of the metal foils ranged from 0.002 to 0.008 in. (0.05 to 0.2 mm). All of these materials gained weight during the testing, and some of the foils became too distorted to use as collection substrates 284. The preferred materials, the Haynes 230 foil and the iron aluminide foil, exhibited the lowest weight gain (0.12 mg). More particularly, the Haynes 230 foil is the preferred material for the collection substrates 282 due to cost and commercial availability. Collection substrates 282 have been made from this alloy and have proven to be stable in flue gas environments.

The cascade impactor 240 can optionally be combined with an alkali vapor collector 16, which will be described in greater detail below, to form a combined particulate and alkali sampling system. In a preferred embodiment, the housing 242 of the cascade impactor is attached to or integral with a housing portion of the alkali vapor collector 16. The housing portion of the alkali vapor collector 16 can comprise mounting means for attachment to the probe 42. In this embodiment, the discharge 368 from the cascade impactor 240 is communicated to an inlet of the alkali vapor collector 16, alkali vapors are collected from the fluid in the alkali vapor collector 16, and the discharge from the alkali vapor collector 16 is communicated to the conduit 64 of the probe 42.

Total-Mass Sampler

The present invention also provides a total-mass sampler 500, which will be described with particular reference to the embodiment depicted in FIG. 25. The total-mass sampler 500 can comprise the particulate sampling means 14 of the sampling system 10 described above, or may find application in a variety of other particular sampling applications. According to a preferred form of the invention, the total-mass sampler 500 generally comprises a housing 242 comprising a precollector portion 244 and an impactor shell 246. The precollector portion 244 preferably comprises an entry nozzle 248, shown in detail in FIG. 23, for isokinetically extracting a portion of fluid 250 containing particulate matter from a process gas or other fluid. The total-mass sampler 500 is particularly adapted for in-situ sampling within a fluid.

The entry nozzle 248 communicates fluid 250 to a plenum 252 within the precollector portion 244, which in turn, communicates fluid to a duct 254 leading into an interior chamber 255 within the impactor shell 246. The sampled fluid 250 is communicated from the duct 254, through a first spacer section 520, to a total-mass particulate collection stage 510. The first spacer section 520 is a generally cylindrical element adapted to be received within the interior chamber 255 of the impactor shell 246. The first spacer section 520 has a top end 522 adapted to abut an end wall of the interior chamber 255, and a bottom end 524 adapted to abut the top of the total-mass particle collection stage 510. The total-mass sampler 500 may also include a second spacer section 530 having an upper end 532 and a lower end 534. The second spacer section 530 is a generally cylindrical element adapted to be received within the interior chamber 255 of the impactor shell 246. The second spacer section 530 is downstream of the first spacer section 520 and preferably has the same external diameter as the first spacer section 520. In this example, the upper end 522 of the second spacer section 550 is adapted to abut the bottom of the total-mass particle collection stage 510 and the lower end 554 is adapted to abut a mounting wall of the support plate 364.

The total-mass sampler 500 may also include at least one temperature-impervious gasket 540, such as a compressed ceramic fiber gasket or other sealing means. Such a gasket 540 may, for example, be provided between an end wall of the interior chamber 255 and the top end 522 of the first spacer section 520 and may, for example, be provided between the mounting wall of the support plate 364 and the lower end 534 of the second spacer section 530.

The total-mass particle collection stage 510 is provided in the interior chamber 255 of the impactor shell 246 and preferably includes a disk-shaped particle collection filter element 512 and a complementarily sized, substantially rigid, disk-shaped filter support plate 516. The particle collection filter element 512 has a lower surface 514. The filter support plate 516 has a top surface 517, an opposing bottom surface 518, and a plurality of perforations extending through the filter support plate 516 from the top surface 517 to the bottom surface 518. The lower surface 515 of the particle collection filter element 512 rests on the top surface 517 of the filter support plate 516 so that the particle collection filter element 512 is supported as fluid 250 impacts and flows through the total-mass particle collection stage 510.

In this example, fluid 250 is distributed from the duct 254 through the first spacer section 520 and over and through the total-mass particle collection stage 510. As one skilled in the art will appreciate, after sampling, the particle collection filter element 512 can then be removed and analyzed by, for example, a laboratory particle size analyzer to determine characteristics such as the particle size distribution and total particulate loading of the particulate matter in the fluid 250.

Figure 25:
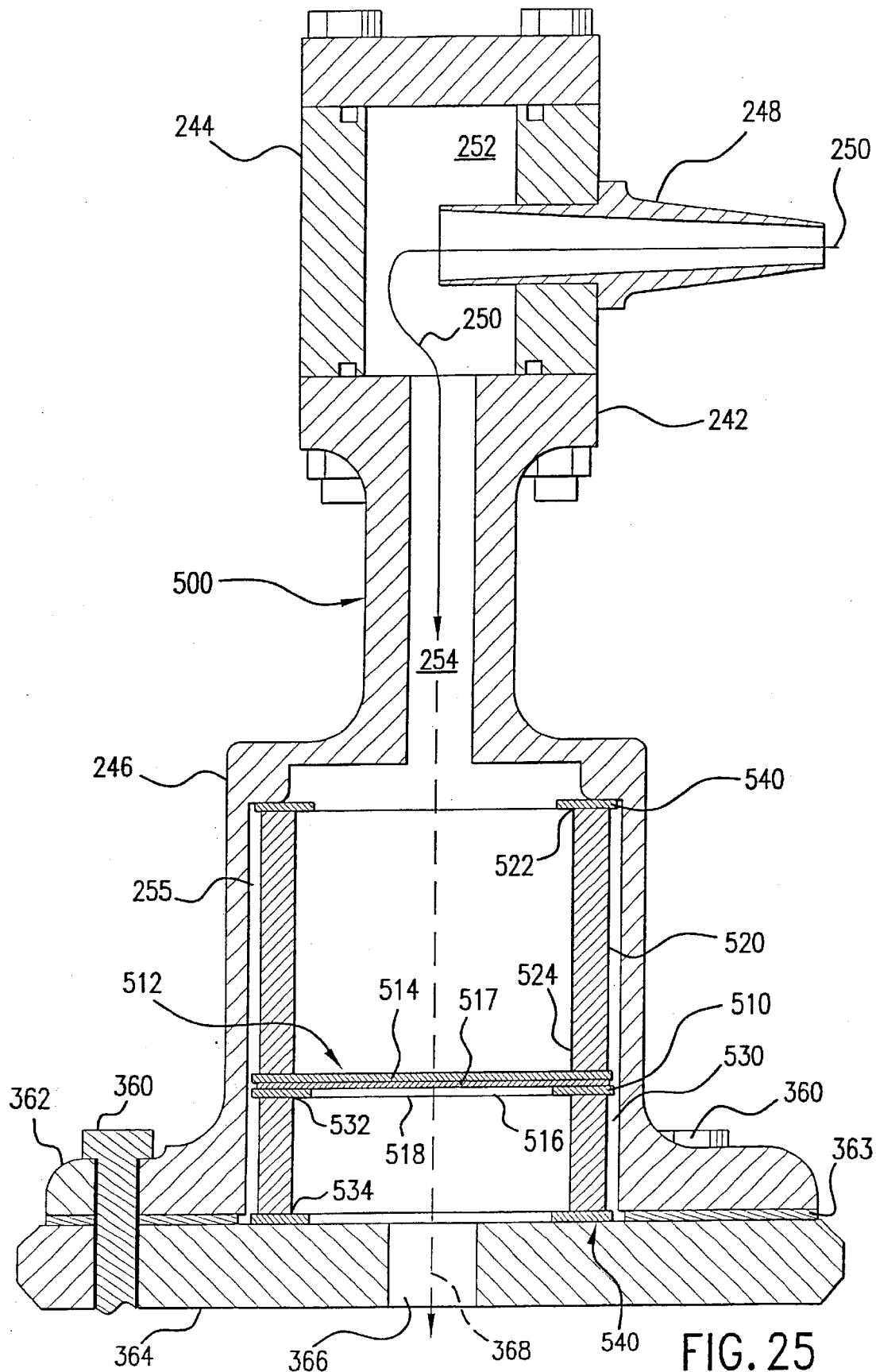
FIG. 25 shows a cross-section view of a total-mass sampler of the present invention.
Figure 26A:
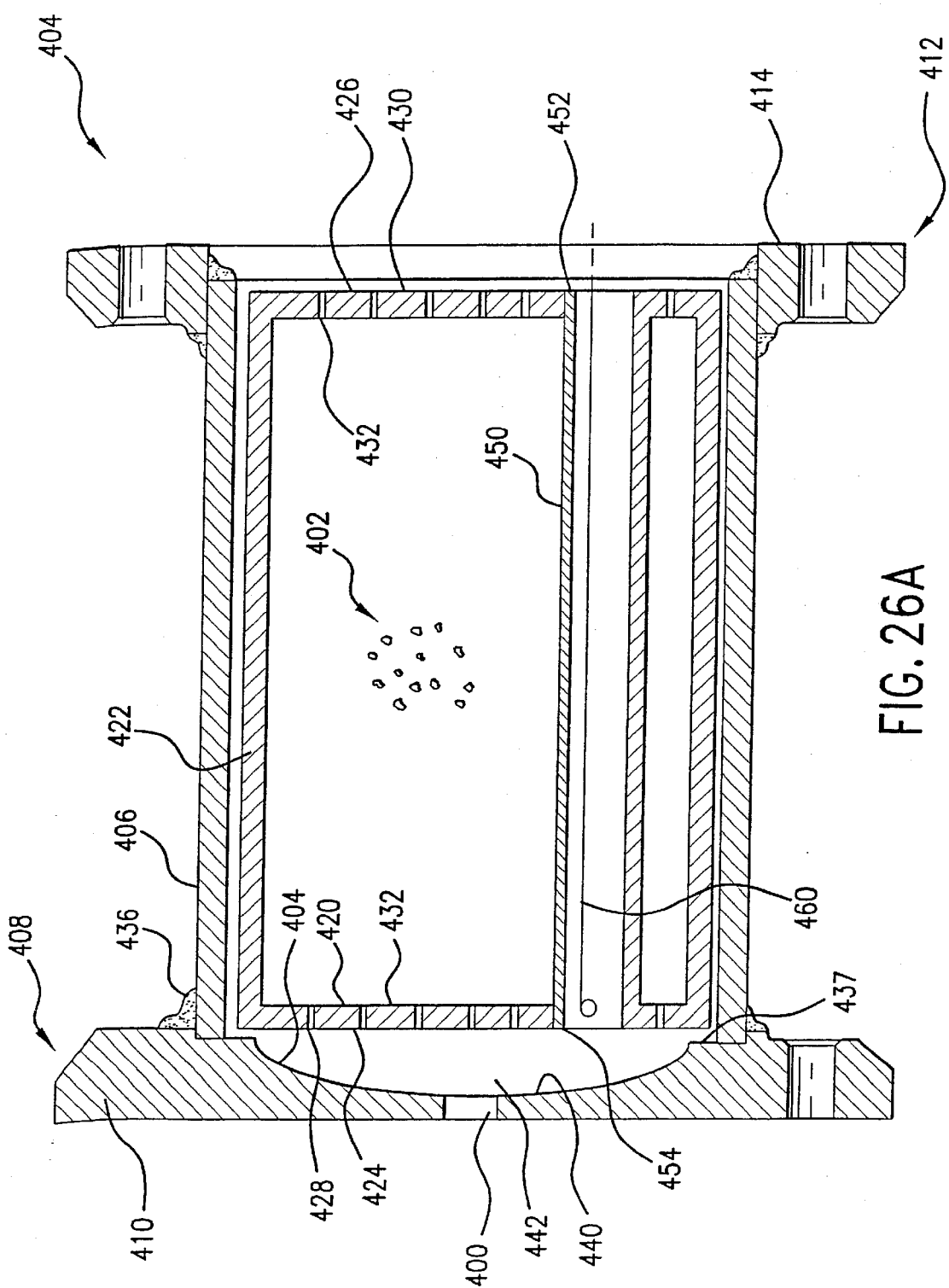
FIGS. 26A–26B show a cross-sectional side and end view, respectively, of a housing component of an alkali vapor collector.
Figure 26B:
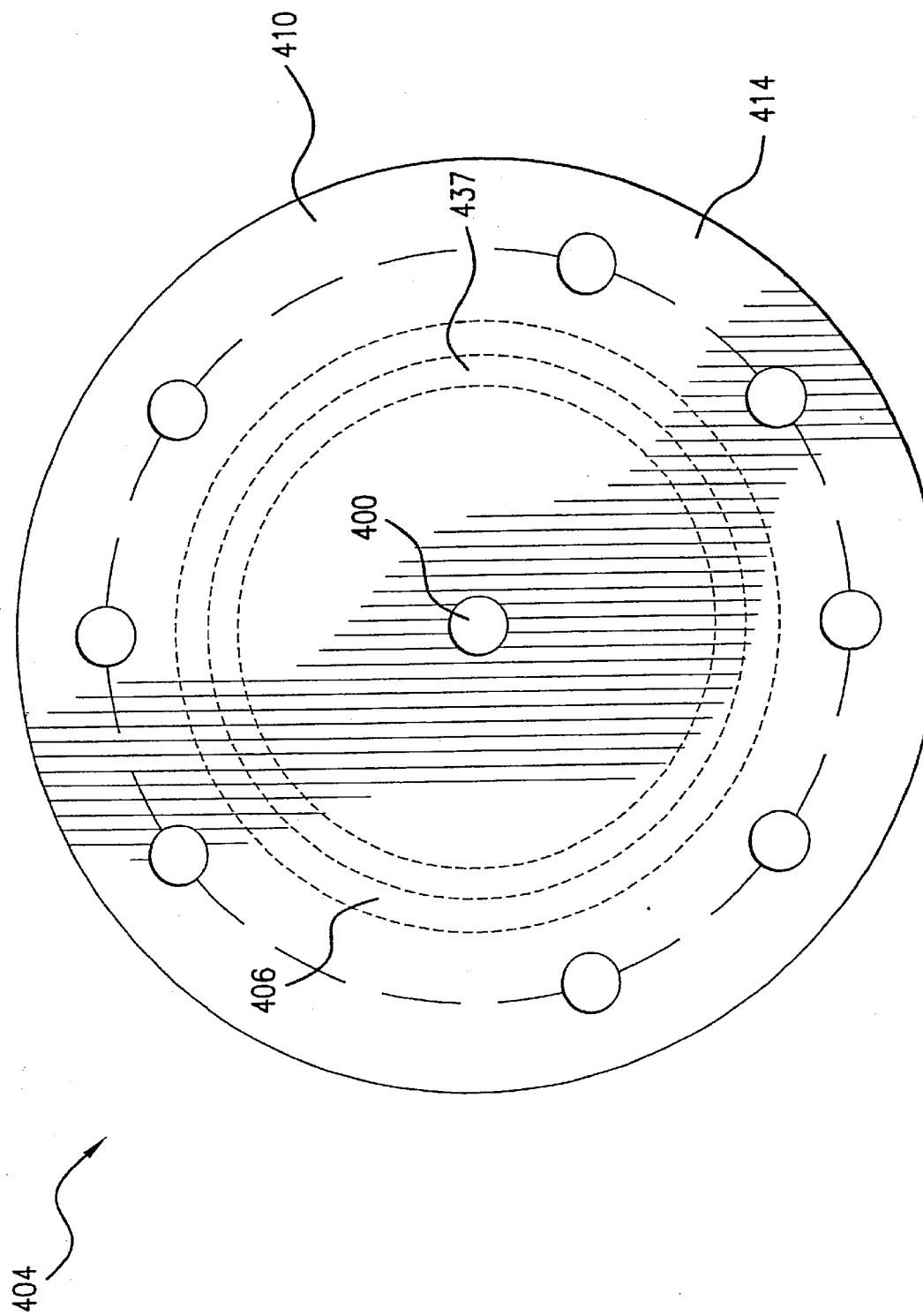

Referring to FIG. 25, the total-mass sampler 500 is preferably assembled by: inserting a gasket 540 into the end wall of the interior chamber 255; placing the top end 522 of the first spacer section 520 against the gasket 540; placing the total-mass particle collection stage 510 onto the bottom end 524 of the first spacer section 520; mounting the upper end 532 of the second spacer section 530 onto the bottom of the total-mass particle collection stage 510; placing an additional gasket 540 onto the bottom end 534 of the second spacer section 530; and securing and sealing the total-mass sampler 500 to the mounting surface of the support plate 364 by attaching the housing 242, preferably via releasable attachment means such as bolts 360 engaging a mounting flange portion 362 of the housing 242, to the support plate 364 or other support means. A passage 366 through the support plate 364 communicates the discharge 368 from the total-mass sampler. The support plate 364 can, for example, comprise a portion of the probe 42 for insertion and retraction into a process fluid 20, and the discharge 368 can be communicated from the total-mass sampler 500 to the conduit 64 of the probe 42.

Sample fluid 250 thus traverses a flowpath through the total-mass sampler 500. The fluid 250 and entrained particulate matter enters the total-mass sampler 500 through the entry nozzle 248, passes through the plenum 252 and the duct 254, through the first spacer section 520, and is distributed for introduction to the total-mass particle collection stage 510. The flowpath passes through the particle collection filter element 512 and particulate matter impacts and is collected on the filter element 512. The fluid 250 then passes through the perforated filter support plate 516, passes through the second spacer section 530, if provided, and is discharged from the total-mass sampler 500.

The preferred materials for fabrication of the impactor shell 246, precollector portion 244, filter support plate 516, and first and second spacer sections 520, 550 are Haynes 556, HR-160, or RA333. An example of a suitable material for constructing the particle collection filter element 512 is Kaowool 2000 because it does not gain or lose a significant amount of weight as a result of the interaction with the flue gas in the absence of particulate matter.

The total-mass sampler 500 can optionally be combined with an alkali vapor collector 16, which will be described in greater detail below, to form a combined particulate and alkali sampling system. In a preferred embodiment, the housing 242 of the total-mass sampler 500 is attached to or integral with a housing portion of the alkali vapor collector 16. The housing portion of the alkali vapor collector 16 can comprise mounting means for attachment to the probe 42. In this embodiment, the discharge 368 from the total-mass sampler 500 is communicated to an inlet of the alkali vapor collector 16, alkali vapors are collected from the fluid in the alkali vapor collector 16, and the discharge from the alkali vapor collector 16 is communicated to the conduit 64 of the probe 42.

Alkali Vapor Collector

The present invention also provides an alkali collector for in-situ collection of alkali vapors from the sampled fluid. With reference to FIGS. 1 and 26A–27C, preferred forms of the alkali vapor collector 16 will be described. As discussed in greater detail above, the alkali vapor collector 16 can be combined with a particulate sampling means 14, such as a cyclone sampler 100, a cascade impactor 240, a total-mass sampler 500, or other samplers. Sampled fluid discharged from the particulate sampling means 14 is introduced into an inlet 400 of the alkali vapor collector 16. The fluid is contacted with an alkali sorbent media 402, such as, for example, activated bauxite or activated alumina, in the alkali vapor collector 16. After a sampling run, the alkali collected on the alkali sorbent media 402 is recovered and analyzed. The alkali sorbent media 402 is preferably in granular, pellet or powder form, thereby increasing surface area available for contact with the fluid. Such an alkali sorbent media 402 is exemplified by the beads of activated bauxite having a nominal size of ⅛ inch to ¼ inch distributed by Alcoa Industrial Chemicals as Product Nos. CL-750 or DD-2 or from Fisher Scientific as Product No. A505-212. An alternative alkali sorbent media 402 is exemplified by the beads of activated alumina having a nominal size of ¼ inch distributed by Porocel Absorbent and Catalysts, Co. as Purocel SRC.

The alkali vapor collector 16 preferably comprises an outer housing 404 having a generally cylindrical wall portion 406, a first end 408 comprising a distal mounting flange 410, and a second end 412 comprising a proximal mounting flange 414. The distal mounting flange 410 can, for example, be adapted to be coupled to a particulate sampling means 14, with the inlet 400 receiving a discharge flow from the particulate sampling means 14. The proximal mounting flange 414 can be adapted to be mounted to the probe 42, or to any external support structure.

In a further preferred embodiment, the alkali vapor collector 16 can further comprise a liner 420 provided between the housing 404 and the alkali sorbent material 402. The liner 420 is preferably formed from a material that is impervious to the fluid sampled. It is further preferred that the liner 420 be nonreactive with alkali vapor so that any alkali that is physically absorbed onto the liner 420 can be easily recovered by rinsing the liner 420 with deionized water. In a most preferred form, the liner 420 is formed from a ceramic material, preferably alumina as it does not react with the alkali vapor. A liner 420 formed of metal may react with the alkali vapor, making recovery of the alkali difficult. The liner 420 serves to protect the housing 404 from corrosion from alkali vapors and other constituents of the fluid, and to facilitate installation and removal of the alkali sorbent material 402. The liner 420 and alkali sorbent material 402 can serve as a replaceable cartridge that can be removed from the housing 404 and replaced when spent.

The liner 420 may preferably comprise a generally cylindrical shell 422 having a proximal end 424 comprising a detachable proximal end cap 428 and a second end 426 comprising a fixedly attached distal end cap 430. The proximal end cap 428 preferably has a plurality of fluid ducts 432 extending therethrough and the distal end cap 430 preferably also has a plurality of fluid ducts 432 extending therethrough. The proximal and distal end caps 428, 430 are preferably reticulated so that, for example, vapor may enter the liner 420 and be brought into contact with the alkali sorbent material 402 contained within the liner 420.

In another further preferred embodiment, the distal mounting flange 410 of the outer housing 404 has an inner surface 434. The inner surface 434 preferably has a flat surfaced bearing section 436 extending toward the interior of the alkali vapor collector 16 and about the circumference of the inner surface 434. As one will observe, the bearing section 436 has an inner diameter that is less than the diameter of the wall portion 406 of the housing 404, thereby forming a circumferentially extending angled lip 437 between the wall portion 406 and the bearing section 436, which assists in providing a desired mechanical stop for the proximal end 424 of the liner 420 when the liner 420 is inserted into the housing 406. The inner surface 434 of the distal mounting flange 410 also preferably has a depression 440 that is preferably centered on the inlet 400 of the collector 16 and that preferably extends to the bearing section. As one skilled in the art will appreciate, the depression 440 within the inner surface 434 will oppose the proximal end cap 428 of the liner 420 and defines a diffuser chamber 442 for the diffusion of vapor entering the alkali vapor collector 16 via inlet 400. The depression 440 is preferably concave in cross-section to form a dome-shaped diffuser chamber 442.

Figure 27A:
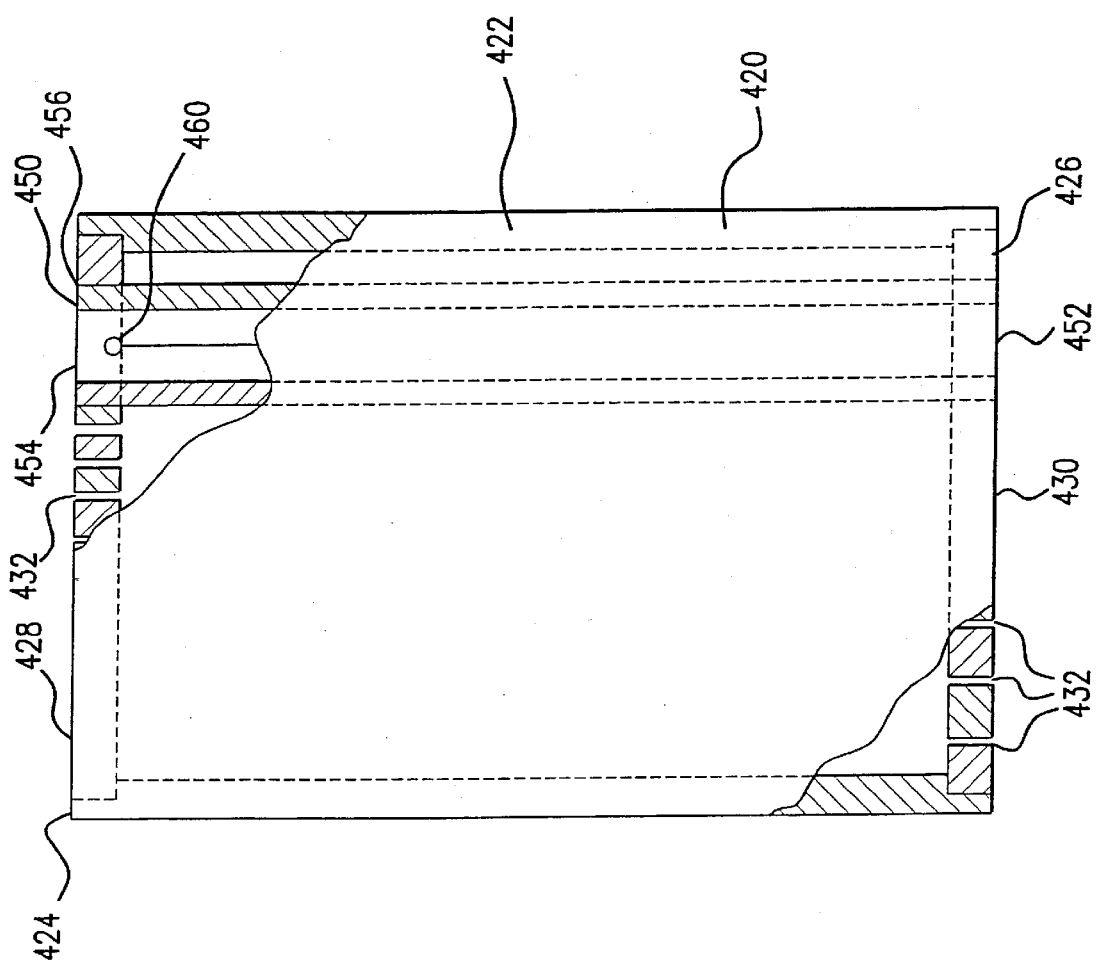
FIGS. 27A–27C show a partial cross-sectional side view, a side view, and a end view, respectively, of a liner component of the alkali vapor collector.
Figure 27C:
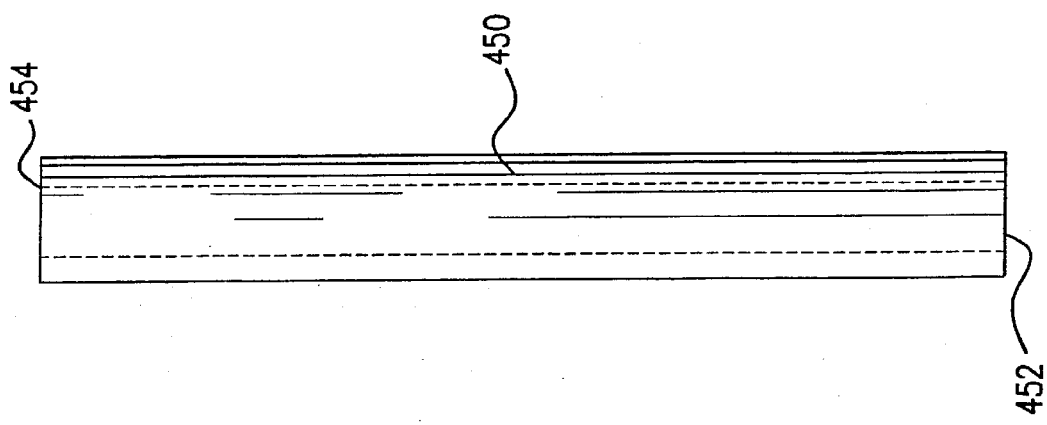
Figure 27B:
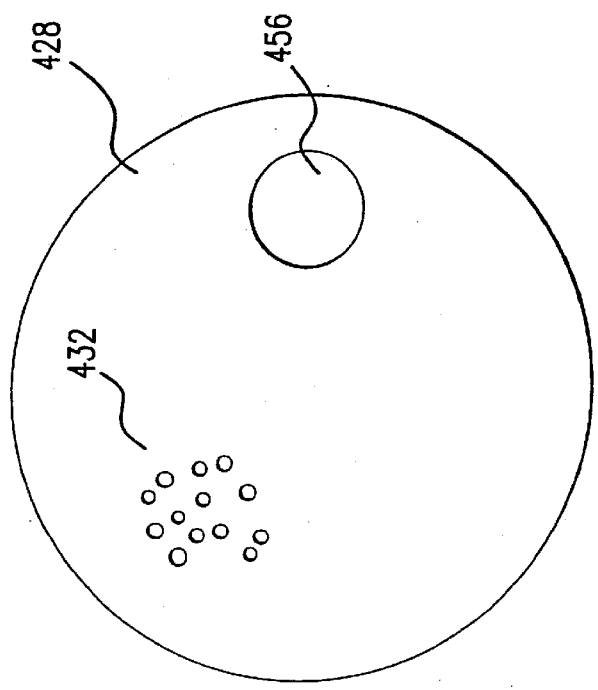

Referring to FIGS. 27A–27C, it is preferred that the liner 420 also have an elongated tube 450 having a closed first end 452 and an open second end 454. It is preferred that the closed first end 452 of the tube 450 be adapted to be fixedly mounted to the distal end cap 430 of the liner 420. It is further preferred that the open second end 454 of the tube 450 extend into and through a bore 456 which extends therethrough the proximal end cap 428 of the liner 420. This allows the tube 450 to be in flow communication with the gas entering the collector 16. A thermocouple 460 is preferably inserted into the interior of the tube 450 via an opening in the closed first end 452 which is subsequently sealed. The thermocouple 460 preferable extends within the tube 450 to near the open second end 454 of the tube 450 and, in combination with the tube 450, acts as a thermowell for the measurement of the temperature of the gas proximate the inlet 400 of the alkali vapor collector 16. Alternatively, the thermocouple 460 may feed though the tube 450 and extend from the open second end 454 into the inlet 400 of the collector 16. It is desired to monitor the temperature of the gas, preferably continuously, proximate the inlet 400 to ensure that the alkali vapor is not condensed out prior to reaching the alkali vapor collector 16.

The sampling system described above may be used in many configurations. For example, the total-mass sampler 500 may be used in with or without the alkali vapor sampler 16, the cyclone sampler 100 may be used with or without the alkali vapor sampler 16, or the cascade impactor 240 may be used with or without the alkali vapor sampler 16.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modification, both as to equipment details and operating procedures can be effected without departing from the scope of the invention itself. Further, it should be understood that, although the present invention has been described with reference to specific details of certain embodiments thereof, it is not intended that such details should be regarded as limitations upon the scope of the invention except as and to the extent that they are included in the accompanying claims.

What is claimed is:

1. A jet plate for a cascade impactor, said jet plate comprising a body portion having a plurality of jet holes extending therethrough, said jet plate further comprising an integral spacer depending from the first surface, wherein the integral spacer comprises a curumferential lip, a first diametrical rib, and a second diametrical rib.

2. The jet plate of claim 1, further comprising an alignment tab projecting radially from said body portion.

* * * * *